(12) United States Patent
Shimura et al.

(10) Patent No.: US 7,672,799 B2
(45) Date of Patent: Mar. 2, 2010

(54) DEFECT INSPECTION APPARATUS AND DEFECT INSPECTION METHOD

(75) Inventors: Kei Shimura, Mito (JP); Minori Noguchi, Joso (JP); Masaaki Ito, Hitachinaka (JP); Kenji Aiko, Hitachinaka (JP); Shuichi Chikamatsu, Konosu (JP); Shigeo Otsuki, Kasama (JP); Shigeru Abe, Kodama (JP); Masayuki Ochi, Kodama (JP); Takuaki Sekiguchi, Honjo (JP); Hiroyuki Yamashita, Fujioka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 112 days.

(21) Appl. No.: 11/846,829

(22) Filed: Aug. 29, 2007

(65) Prior Publication Data

US 2008/0059094 A1    Mar. 6, 2008

(30) Foreign Application Priority Data

Aug. 30, 2006    (JP) ............................. 2006-234600

(51) Int. Cl.
G06F 19/00    (2006.01)
G01N 21/00    (2006.01)

(52) U.S. Cl. ..................................... 702/81; 356/237.2
(58) Field of Classification Search .................... 702/81, 702/83; 356/237.2, 237.5
See application file for complete search history.

(56) References Cited

U.S. PATENT DOCUMENTS 5,463,459 A * 10/1995 Morioka et al. .......... 356/237.5

6,411,377 B1 * 6/2002 Noguchi et al. .......... 356/237.4

FOREIGN PATENT DOCUMENTS

| JP | 62-89336 A | 4/1987 |
|---|---|---|
| JP | 63-135848 A | 6/1988 |
| JP | 1-117024 A | 5/1989 |
| JP | 1-250847 A | 10/1989 |
| JP | 5-218163 A | 8/1993 |
| JP | 6-258239 A | 9/1994 |
| JP | 6-324003 A | 11/1994 |
| JP | 8-210989 A | 8/1996 |
| JP | 8-271437 A | 10/1996 |
| JP | 2000-105203 A | 4/2000 |
| JP | 3566589 B2 | 6/2004 |

* cited by examiner

*Primary Examiner*—Bryan Bui
(74) *Attorney, Agent, or Firm*—Crowell & Moring LLP

(57) ABSTRACT

A defect inspection apparatus includes: stages each mounting an inspecting object on which a circuit pattern having a group of parallel lines is formed, and each running perpendicular or parallel to the group of lines; an illumination optical system which illuminating a surface of the inspecting object with a slit beam being slit light so that a longitudinal direction of the slit beam is substantially perpendicular to the running directions of the stages, and which has a first inclined angle formed by the direction of the group of lines and a projection line, of an optical axis of the slit beam, to the inspecting object; a spatial filter that shields or transmits reflected and scattered light of the inspecting object according to a difference in distribution of orientation; and a detection optical system that detects the reflected and scattered light transmitted through the spatial filter by image sensors. Moreover, the illumination optical system illuminates the inspecting object with another slit beam from a direction opposite to an incident direction of the slit beam on a plane.

17 Claims, 17 Drawing Sheets

DEFECT INSPECTION APPARATUS AND DEFECT INSPECTION METHOD

CLAIM OF PRIORITY

The present application claims priority from Japanese application JP 2006-234600 filed on Aug. 30, 2006, the content of which is hereby incorporated by reference into this application.

BACKGROUND OF THE INVENTION

1. Technical Field

The present invention relates to a defect inspection apparatus and a defect inspection method for inspecting a defect of an inspecting object on which a circuit pattern including group of lines is formed.

2. Background Art

In a semiconductor manufacturing process, foreign materials on a surface of a semiconductor substrate (wafer) will cause insulation failure of wiring, failure of short-circuiting or the like, and fine foreign materials will cause insulation failure of capacitor, breakage of a gate oxide film or the like. These foreign materials include: those that are generated from a movable section of a transfer apparatus; those that are generated from a human body; those that are reaction-generated in a processing apparatus by process gas; and those that are mixed in chemicals and material and they contaminate the surface of a semiconductor substrate in various states due to various causes. Moreover, even in a manufacturing process for liquid crystal display elements, if the foreign materials contaminate the pattern to cause some sort of defect, the liquid crystal display elements will not be used as display elements. Furthermore, the same circumstance can be expected in a manufacturing process for printed boards, and contamination by of foreign materials is responsible for short-circuiting of pattern and contact failure.

Japanese Patent Application Laid-open Publication Nos. Sho 62-89336 (FIG. 1, page 5, upper right column), Sho 63-135848 (FIG. 1), Hei 1-117024 (Claim 4), Hei 1-250847, Hei 6-258239, Hei 6-324003, Hei 8-210989, Hei 8-271437, and 2000-105203 disclose the techniques of detecting such foreign materials adhering to the surface of the semiconductor substrate. For example, in the technique disclosed in JP-A No. Sho 62-89336, a semiconductor substrate is irradiated with a laser to detect scattered light, which is generated from the foreign material when the foreign material adheres to the semiconductor substrate, and the detected result is compared with the preceding inspection result of the same type of semiconductor substrate. In this way, this technique eliminates a false alarm, which might be caused due to pattern, enables inspection of foreign materials and defects with high sensitivity and high reliability. Moreover, in the technique disclosed in JP-A No. Sho 63-135848, the semiconductor substrate is irradiated with a laser to detect scattered light from the foreign material on the surface of the semiconductor, and the detected foreign material is analyzed by analysis technique such as laser photoluminescence or secondary X-ray analysis (XMR).

Furthermore, as a technique for inspecting a foreign material, there is known a method of emphatically detecting a foreign material or defect having no repeatability while the surface of a semiconductor substrate (wafer) is irradiated with coherent light, and also while light emitted from a repetition pattern on the wafer is removed through a spatial filter. Moreover, JP-A No. Hei 1-117024 (Claim 4) discloses a foreign material inspection apparatus that detects a foreign material in such a way that a main group of lines of a circuit pattern formed on a wafer surface is irradiated with illumination light from a direction inclined at 45 degree to a direction of the main group of lines, while zero-order diffracted light from the main group of lines is prevented from being inputted to an aperture of an objective lens. JP-A No. Hei 1-117024 also discloses that a group of lines other than the main group of lines is shielded through the spatial filter. Furthermore, JP-A Nos. Hei 1-250847, Hei 6-258239, Hei 6-324003, Hei 8-210989, Hei 8-271437, and 2000-105203 disclose techniques relating to an apparatus for inspecting a defect such as a foreign material and a method for the same. In addition, JP-A Nos. Hei 5-218163 and Hei 6-258239 (FIG. 3) disclose an example of spatial filters.

SUMMARY OF THE INVENTION

However, in the techniques disclosed in the aforementioned patent documents, it is not possible to easily perform high-speed and high-sensitive detection of the defect such as a fine foreign material on the semiconductor substrate where a repetition pattern and a non-repetition pattern are mixed. In other words, in the aforementioned patent documents, there is a problem that detection sensitivity (minimum detectable foreign material size) is considerably reduced on portions other than the repetition portion such as a memory cell portion. Furthermore, there is a problem that sensitivity is considerably reduced on an oxide film through which illumination light is transmitted, thus making it impossible to detect a defect such as a fine foreign material.

Additionally, in the aforementioned patent documents, distinction between a mass production startup and a mass production line in the semiconductor manufacturing process is not made, and the inspection apparatus used in the mass production startup operation is directly applied to the mass production line. In the mass production line, although it is necessary to sense occurrence of a foreign material as soon as possible and take necessary measures thereagainst, the scale of the defect inspection apparatus described in the patent documents is configured such that the apparatus scale is increased, and that the apparatus has to be installed independently. For this reason, it is necessary for semiconductor substrates, liquid crystal display element substrates and print substrates that are processed in the manufacturing line to be brought into the inspection apparatus installation area for undergoing inspection of foreign materials and defects. Accordingly, much time is required to transfer these substrates and to inspect foreign materials and defects, thus making it difficult to inspect all the substrates and obtain a sufficient inspection frequency even in a sampling inspection. In addition, such a configuration requires much manpower.

By the way, regarding the semiconductor defects, there are many types of defects such as difference in size, projection, dent, etc., and classification of these defects is required. Regarding this point, in the aforementioned patent documents, in a case of illumination inclined to the normal direction of the semiconductor substrate, only scattered light from the opposite side to the illumination incident direction is detected, so that the number of types of defects to be classified is limited.

Accordingly, an object of the present invention is to provide a defect inspection apparatus and its method that are capable of increasing a defect capture rate and a defect classification performance.

In order to solve the aforementioned problems, a defect inspection apparatus of the present invention includes: a stage that runs with an inspecting object mounted thereon, the inspecting object having a circuit pattern including a group of lines parallel to each other formed therein; an illumination optical system that illuminates a surface of the inspecting object with a slit beam being a slit light to have a first inclined angle formed by the direction of the group of lines and a projection line, of an optical axis of the slit beam, to the inspecting object; a detection optical system that detects reflected and scattered light from the inspecting object by an image sensor; a signal processing section that extracts a signal indicating a defect of a foreign material or the like in response to a signal detected by the image sensor of the detection optical system; and a defect classifying section that classifies the defect according to a difference in distribution of orientation of reflected and scattered light of the inspecting object. Moreover, the illumination optical system illuminates the inspecting object with another slit beam from a direction opposite to an incident direction of the slit beam on a plane.

According to the above, the slit beam is inclined in such a way to form the first inclined angle by the direction of the group of lines and the projection line to the inspecting object, enters the inspecting object, and is reflected and diffracted by the circuit pattern. Since the slit beam is inclined, it is possible to classify the defect that reflects and scatters light in this direction. Moreover, illumination of the inspecting object with another slit beam from a direction opposite to an incident direction of the slit beam on a plane or separation of light into forward scattered light and backward scattered light allows an increase in the number of types of defects to be classified.

According to the present invention, it is possible to increase a defect capture rate and a defect classification performance.

BRIEF DESCRIPTION OF THE DRAWINGS

FIG. 17A is a diagram illustrating a relationship between a wafer and a pixel, and FIG. 17B is a view illustrating a relationship between a chip and a pixel, each.

DESCRIPTION OF THE PREFERRED EMBODIMENTS OF THE INVENTION (Inspecting Object)

First, an explanation will be given of an inspecting object in which a defect is inspected by using a defect inspection apparatus of the present invention.

Figure 1:
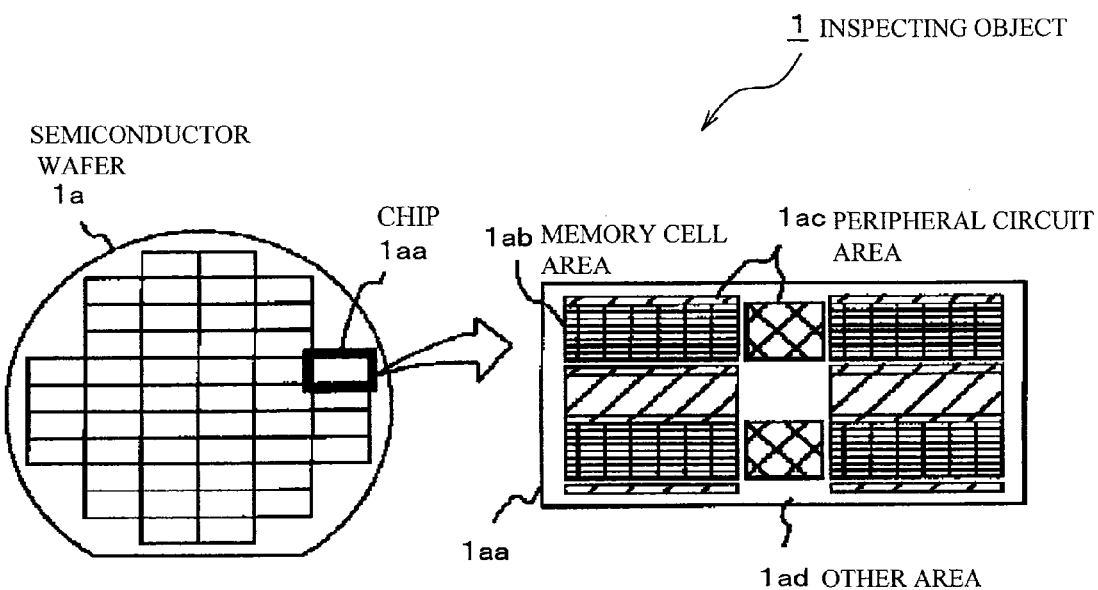
FIG. 1 is a view illustrating a semiconductor wafer of one example of an inspecting object that is inspected by a defect inspection apparatus according to one embodiment of the present invention.

FIG. 1 shows one example of an inspecting object 1, which is a disc-like semiconductor wafer 1*a* where chips 1*aa*, each formed of a memory LSI, are two-dimensionally arranged with a predetermined distance. The chip 1*aa* is composed of mainly a memory cell area 1*ab*, a peripheral circuit area 1*ac* including a decoder, a control circuit and the like, and other area 1*ad*. The memory cell area 1*ab* is formed in such a way that a memory cell pattern having a minimum line width of, for example, on the order of 0.05 to 0.3 μm is two-dimensionally and regularly (repeatedly) formed. However, in the peripheral circuit area 1*ac*, a non-repetition pattern having a minimum line width of, for example, on the order of 0.1 to 0.4 μm is formed. Moreover, the other area 1*ad* includes, for example, a bonding area (having a minimum line width of, for example, on the order of 10 μm and having almost no pattern).

Figure 2:
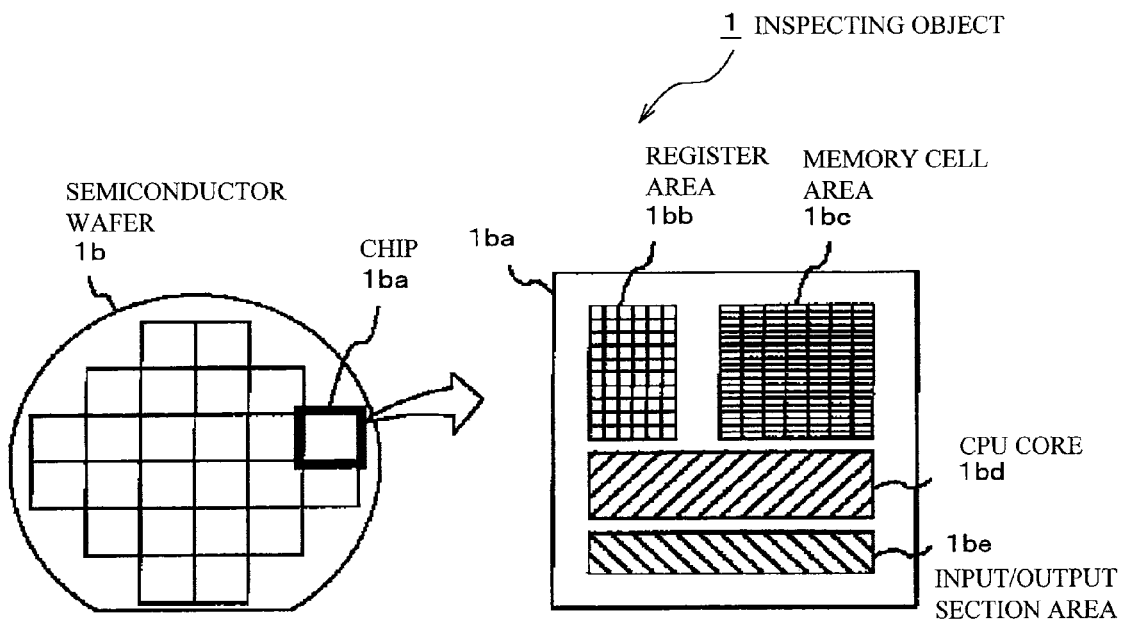
FIG. 2 is a view illustrating a semiconductor wafer of another example of an inspecting object that is inspected by a defect inspection apparatus according to one embodiment of the present invention.

FIG. 2 shows another example of the inspecting object 1, which is a semiconductor wafer 1*b* where chips 1*ba*, each formed of an LSI such as a micro computer, are two-dimensionally arranged with a predetermined distance. Then, the chip 1*ba* is composed of mainly a register area 1*bb*, a memory section area 1*bc*, a CPU core section area 1*bd*, and an input/output section area 1*be*. In addition, FIG. 2 conceptually shows arrangement of the memory section area 1*bc*, the CPU core section area 1*bd* and the input/output section area 1*be*. The register area 1*bb* and the memory section area 1*bc* are formed in such a way that a pattern having a minimum line width of on the order of 0.05 to 0.3 μm is two-dimensionally and regularly (repeatedly) formed. In the CPU core section area 1*bd* and the input/output section area 1*be*, a non-repetition pattern having a minimum line width of on the order of 0.05 to 0.3 μm is formed. As mentioned above, in the inspecting object 1, such as the semiconductor wafer, for example, the chips are regularly arranged, while each chip includes the minimum line widths different among areas, and the pattern being regularly repeated, non-repeated, or no pattern being formed.

First Embodiment

The defect inspection apparatus according to one embodiment of the present invention illuminates the inspecting object 1 with a laser beam and receives scattered light caused by a defect such as a foreign material existing on a pattern area. In this case, a spatial filter is provided to prevent zero-order diffracted light of a circuit pattern (linear pattern), which is formed of a group of lines parallel to each other on a non-repetition pattern area in the chip, from entering an entrance pupil of an objective lens. At this time, the defect inspection apparatus simultaneously emits light from a direction opposite to the direction of illumination light, and detects both forward-scattered light and backward-scattered light. This allows classification that regards asymmetry of the defect as a characteristic and allows classification between a defect having strong forward scatter and a defect having strong backward scatter.

Moreover, the defect inspection apparatus detects a signal subjected to scattered light and calculates position coordinates of the defect. Additionally, in the case of the inspecting object 1, even if a variation occurs in a background signal by a subtle difference in the process that is not regarded as a defect and noise caused at the time of detection, the defect inspection apparatus sets a threshold for extracting a defect such as a foreign material according to this variation, thereby improving detection sensitivity of the defect such as the foreign material and throughput thereof.

The defect inspection apparatus according to one embodiment of the present invention will be explained by using a configuration view in FIG. 3.

Figure 3:
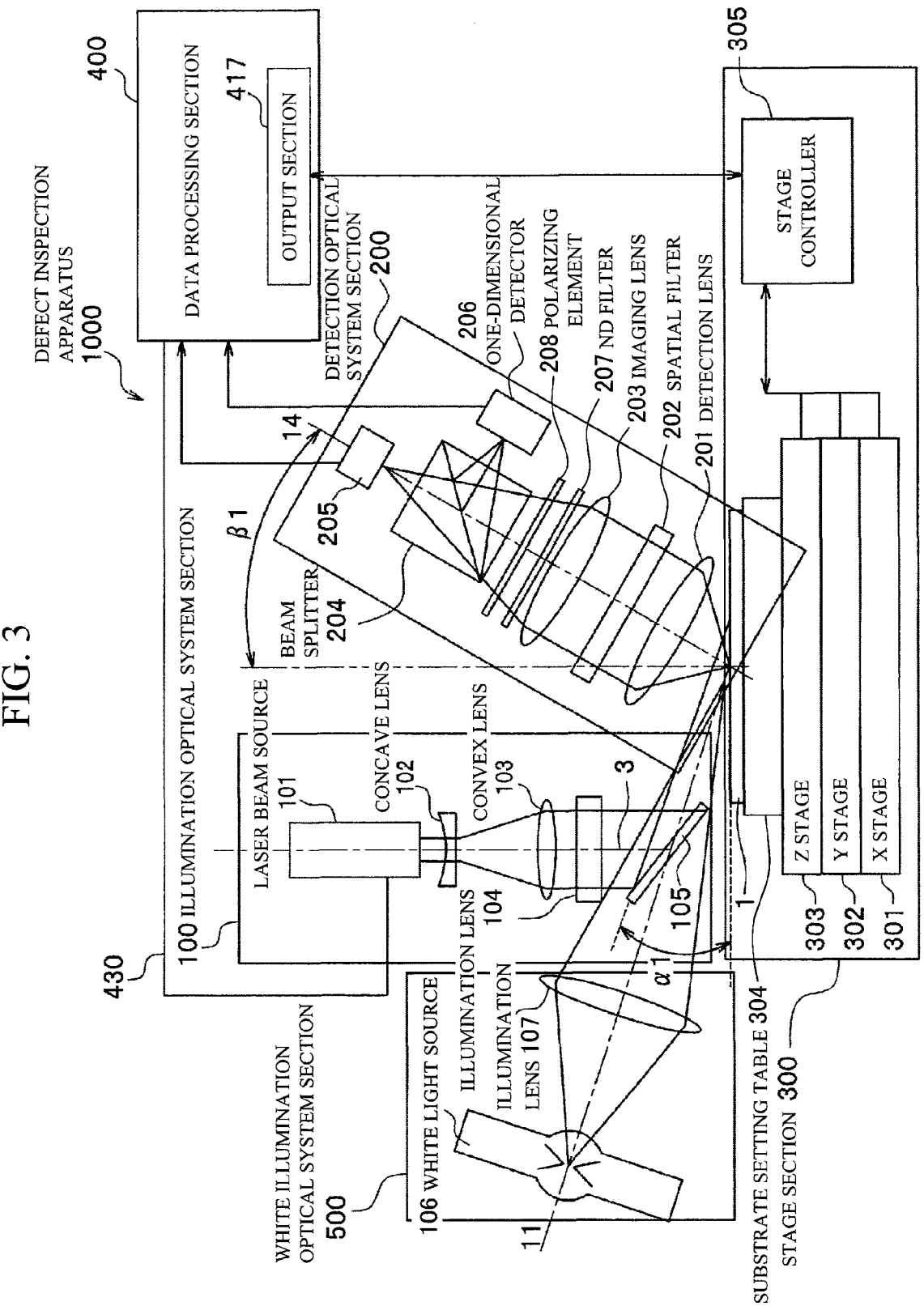
FIG. 3 is a configuration view of a defect inspection apparatus according to one embodiment of the present invention.

In FIG. 3, a defect inspection apparatus 1000 includes an illumination optical system section 100, a detection optical system section 200, a white illumination optical system section 500, a stage section 300, and a data processing section 400.

The stage section 300 includes a substrate setting table 304, an X stage 301, a Y stage 302, a Z stage 303, and a stage controller 305 that controls these stages, and the substrate setting table 304 on which the inspecting object 1 is mounted moves to any position in x, y, and z directions.

The illumination optical system section 100 includes a laser beam source 101, a concave lens 102, a convex lens 103, an illumination lens 104 and a mirror 105, and a parallel light emitted from the laser beam source 101 is condensed through a beam expander, which is composed of the concave lens 102 and the convex lens 103, and the illumination lens 104. Thereafter, the inspecting object 1 is irradiated with the condensed light through the mirror 105.

The laser beam source 101 emits a circular coherent light beam. It is desirable to use a laser beam source of a 532 nm wavelength which is a second harmonics of a high power YAG laser or a fiber laser, more preferably a 355 nm or 266 nm which are the third and the fourth harmonics, furthermore preferably a wavelength of around 200 mn, which is the fourth harmonics of a high power semiconductor laser. The reason is that since a scattering coefficient of Rayleigh scattering is inversely proportional to the fourth power of wavelength, a shorter wavelength is preferably used in order to detect a defect smaller than the wavelength.

The illumination lens 104 focuses a circular laser beam in a y direction to form a slit beam 3 collimated in an x direction (FIG. 4) relative to illumination from an oblique angle (including both inclinations of α1 and φ1). For example, a cylindrical lens is placed in such a way to be parallel to a surface of the inspecting object 1 and have a curved surface whose central axis is parallel to the x direction, whereby an illumination beam enters the cylindrical lens from an inclined direction. This makes it possible to obtain a diffracted light pattern from a circuit pattern where main group of lines are directed in the x direction and y direction and shield light by a spatial filter 202. In addition, as a matter of course, this diffraction is caused by overlapping reflected light on the inspecting object 1.

Figure 4:
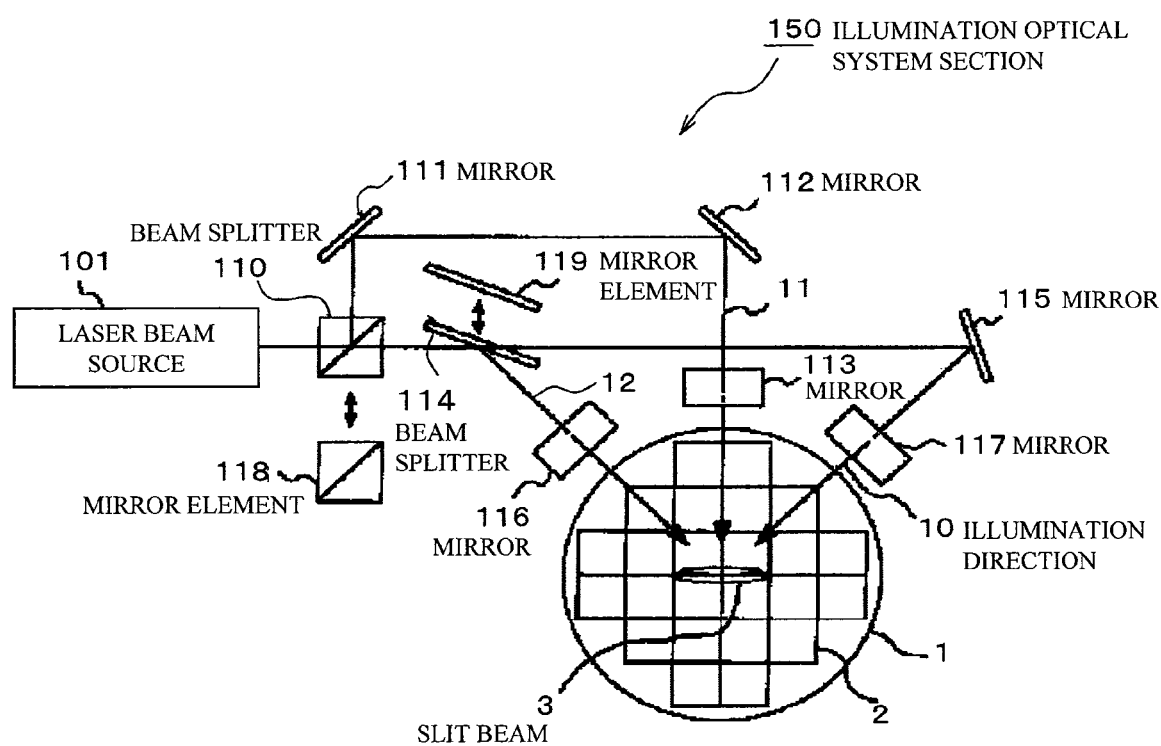
FIG. 4 is a configuration view of an illumination optical system section that illuminates an inspecting object from three directions.

In the present embodiment, the coherent light emitted from the laser beam light source 101 is increased in its beam diameter through the beam expander which is composed of the concave lens 102 and the convex lens 103, and enters the illumination lens 104. The illumination lens 104 outputs illumination light in a collimated form since no lens effect is provided in the x direction, and light is condensed in the y direction by a curvature of the illumination lens 104, so that a slit beam 3 is formed (FIG. 4). The surface of the inspecting object 1 is irradiated with the slit beam 3 through the mirror 105. Then, the reflected and diffracted light (or scattered light) is emitted from the surface of the inspecting object 1, the circuit pattern, and the defect such as the foreign material.

The white illumination optical system section 500 includes a white light source 106 which is a discharge lamp of such as Xe, Hg—Xe, etc., and the illumination lens 107 that condenses radiation light from a point source, and irradiates the inspecting object 1 with incoherent light. Note that the inspecting object 1 can be irradiated with light from the white light source 106 through an optical fiber bundle.

The detection optical system section 200 includes a detection lens 201, a spatial filter 202, an imaging lens 203, a ND (Neutral Density) filter 207, a beam splitter 204, a polarizing element 208, and one-dimensional detectors (image sensors) 205 and 206 such as a TDI (Time Delay Integration) sensor, and an optical axis of a detection direction 14 is inclined at an angle β1 relative to a normal direction of the inspecting object 1. Note that the TDI sensor of anti-blooming type is preferably used, and this allows inspection of the defect such as the foreign material in the vicinity of a saturation region. The anti-blooming type image sensor includes a storage section that stores an electrical charge generated by light receiving. When the stored charges exceed a certain amount, the charge flowing section makes the charges exceeded the certain amount flow. The reading section reads charges stored in the range up to the certain amount.

The detection optical system section 200 is configured to detect light (scattered light, diffracted light) emitted from the inspecting object 1 by using the one-dimensional detectors 205 and 206 through the detection lens 201 where an objective lens is used as an example, the spatial filter 202 that shields a Fourier transformed image due to reflected and diffracted light from the repetition pattern, the imaging lens 203, the ND filter 207 that adjusts an amount of light regardless of the wavelength band, the polarizing element 208 and the beam splitter 204. Note that the detection lens 201 and the imaging lens 203 can be formed as a lens group in which a plurality of lenses is combined. It should be noted that the order of the ND filter 207, the polarizing element 208 and the beam splitter 204 does not have to be in the order mentioned above.

For example, if the DN filter 207 is placed after the beam splitter 204, it is possible to control intensity of light entering two one-dimensional detectors 205 and 206 independently. Moreover, transmittance and reflectance of the beam splitter 204 does not have to be 50%. For example, if one of the transmittance and reflectance is 1% and the other is 99%, light having intensity of about 1/100 enters one detector, and using signals thus obtained from two detectors each receiving light with a different intensity makes it possible to improve an apparent dynamic range of the detector. Accordingly, in the data processing section 400, the signal obtained from the one-dimensional detector 205 and the signal obtained from the one-dimensional detector 206 are used, thereby making it possible to obtain a detection signal having the improved dynamic range from the defect such as the foreign material.

Particularly, in the signal obtained when the one-dimensional detectors 205 and 206 receive light with a high intensity, a component indicating a defect with a high intensity is emphasized, while in the signal obtained when the one-dimensional detectors 205 and 206 receive light with a low intensity, a component close to a background with a small intensity is emphasized. Accordingly, calculating a correlation between both signals, such as a ratio therebetween, makes it possible to improve the dynamic range of the signal indicating the defect. Moreover, illumination (power) of beam luminous flux irradiated from the illumination optical system section 100 such as the laser beam source 101 is controlled, thereby making it possible to change the dynamic range and to omit the beam splitter 204 and the one-dimensional detector 206.

FIG. 4 is a specific configuration view of an illumination optical system section 150 that can be used in place of the illumination optical system section 100 in FIG. 3. The illumination optical system section 150 is configured to illuminate the inspecting object 1 from three illumination directions 10, 11, and 12 through mirrors 117, 113, 116. The laser beam emitted from the laser beam source 101 is divided into two optical paths by a beam splitter 110 such as a half mirror. One of the divided beams is reflected by mirrors 111 and 112, and an illumination beam from the illumination direction 11 can be obtained through the mirror 113. On the other hand, the other divided beam moves to a beam splitter 114 such as a half mirror. One of the beams divided by the beam splitter 114 is reflected by a mirror 115, and an illumination beam from an illumination direction 10 can be obtained by a mirror 117. Furthermore, the other beam divided by the beam splitter 114 passes through the mirror 116, so that an illumination beam from the illumination direction 12 can be obtained.

By the way, illumination from only the illumination direction 11 can be achieved by switching from the beam splitter 110 to a mirror element 118. Moreover, illumination from only the illumination direction 10 and the illumination direction 12 can be achieved by removing the beam splitter 110 from the optical path or by changing the beam splitter 110 to an optical element allowing light to pass therethrough. Furthermore, illumination from only one of the illumination direction 10 and the illumination direction 12, for example, the illumination direction 12, can be achieved by changing the beam splitter 114 to a mirror element 119.

First of all, an explanation will be given of the case where the direction of the detection optical system section 200 is set to a normal direction of the surface of the inspecting object 1, that is, an inclined angle $\beta 1=0$ of an optical axis of the detection optical system section 200 shown in FIG. 3. The spatial filter 202 is placed at a spatial frequency region of the detection lens 201, that is, a position of a Fourier transform surface, in order to shield the Fourier transformed image generated by the reflected and diffracted light from the repetition pattern. Furthermore, when the illumination optical system section 100 provides polarized illumination, the polarizing element 208 shields a polarized component due to reflected and scattered light generated from an edge of the circuit pattern and transmits part of the polarized component due to reflected and scattered light generated from a defect such as a foreign material. It should be noted that the polarizing element 208 is not always an essential structural element.

Figure 5:
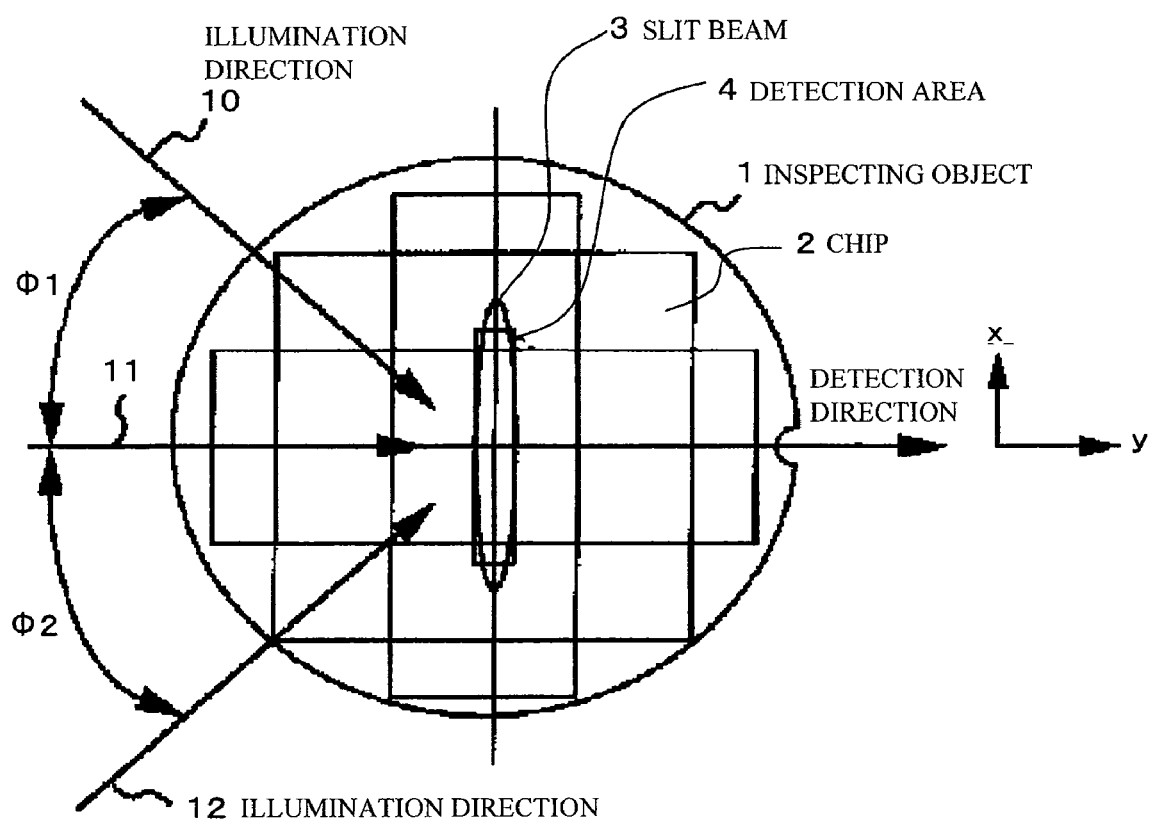
FIG. 5 is a view illustrating a relationship between illumination direction and detection area.

FIG. 5 is a plane view illustrating a relationship between illumination with the slit beam 3 and the scanning direction (y-direction) due to one-dimensional detectors 205 and 206 such as the TDI sensor. FIG. 5 shows the slit beam 3 with which the surface of the inspecting object 1 on which a pattern of a chip 2 is formed is illuminated, and the detection area 4 due to the detection optical systems of one-dimensional detectors 205 and 206. Moreover, the slit beam 3 provides illumination from three directions including the illumination direction 11, the illumination direction 10 separated from the illumination direction 11 by an angle $\phi 1$ and the illumination direction 12 separated from the illumination direction 11 by an angle $\phi 2$. Furthermore, the detection area 4 is an area where an image is formed on the one-dimensional detectors 205 and 206 by the detection lens 201 that forms a relay lens and the imaging lens 203. Additionally, the detection area 4 shows a light receiving area for the one-dimensional detectors 205 and 206 such as the TDI sensor.

FIG. 5 is a view illustrating a state in which the inspecting object 1 is irradiated with light from the illumination optical system section 150. The illumination optical system section 150 irradiates the inspecting object 1 with the slit beam 3 as an illumination area from three illumination directions 10, 11 and 12 on a plane to set the longitudinal direction of the slit beam 3 to the array direction of chips 2.

At this time, illumination light is shaped to the slit beam 3 to achieve speedup of defect inspection of such as a foreign material. More specifically, the longitudinal direction of the slit beam 3 is directed to the array direction of chips relative to the inspecting object 1 and is directed perpendicular to a scanning direction y of the Y stage 302, thereby allowing an integration direction of the one-dimensional detectors 205 and 206 and a stage running direction to be maintained in parallel to each other, and therefore to making it possible to use the TDI sensor. This makes it possible to simplify comparison in image signal between chips and to easily perform calculation of coordinates of the defect position, resulting in achieving speedup of the defect inspection of such as the foreign material.

As shown in FIG. 5, the slit beam 3 illuminates the surface of the inspecting object 1 on which chips 2 are arranged in the x direction of the scanning direction of the X stage 301 (FIG. 3) and the y direction of the scanning direction of the Y stage 302 (FIG. 3). At this time, as shown in FIG. 5, the slit beam 3 illuminates narrowly in the scanning direction y of the Y stage 302 and widely in the perpendicular direction x (scanning direction of the X stage 301). This enables the slit beam 3 to be applied in such way to form an image of a light source in the y direction and to form a parallel light in the x direction. Note that illumination of slit beams 3 from three illumination directions 10, 11 and 12 can be performed individually, and illumination from two illumination directions 10 and 12 can be performed simultaneously.

Figure 6:
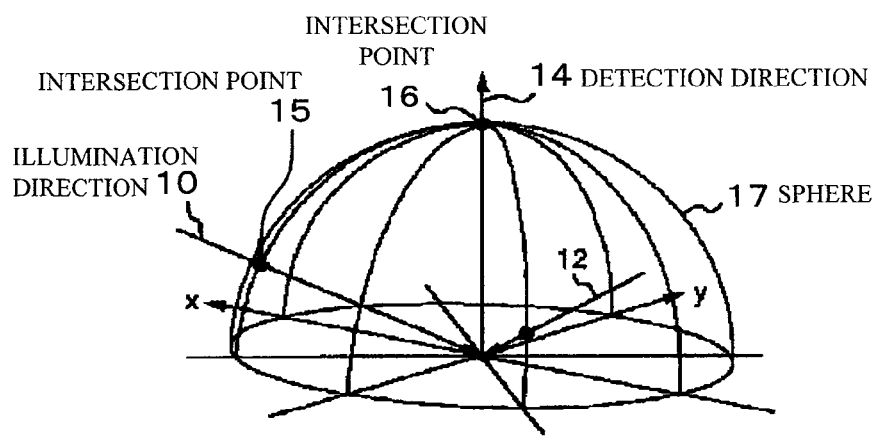
FIGS. 6A and 6B are perspective views each illustrating an illumination direction and a detection direction.
Figure 6:
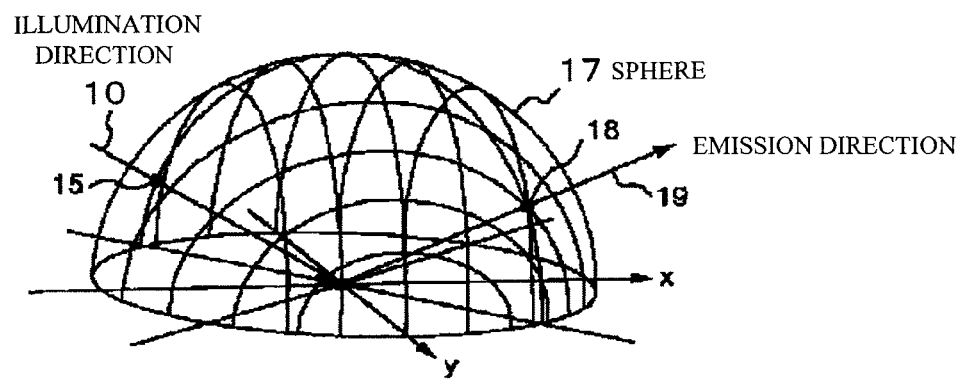

More detailed explanation will be next given of a relationship between the slit beam 3 and the detection optical system section 200. FIG. 6A is a view for explaining FIG. 5 supplementary and shows a relationship between the illumination direction 10 and the detection direction 14 (showing the case of the normal direction of the surface of the wafer) on the basis of x and y axes. In the figure, a sphere 17 is imaginarily formed to review an aperture position of the detection lens 201 (FIG. 3) of the detection optical system section 200. An intersection point of the sphere 17 and the illumination direction 10 is an intersection point 15, and an intersection point of the sphere 17 and the detection direction 14 is an intersection point 16.

FIG. 6B is a view illustrating an emission direction of diffracted light when illumination is performed from the illumination direction 10. In a state where an intersection point 18 of an emission direction 19 of a specular reflection of the illumination 10 and the sphere 17 is zero-order light, diffracted light is emitted in a direction of an edge of a cone having an illumination point as a vertex and extending from the center in the pattern directions (x direction and y direction) as shown in FIG. 6B. As a result, loci of the intersection points with the sphere 17 are on the circumference of a bottom surface of the cone. Accordingly, when viewed from the normal direction, the loci are straight lines parallel to an x axis and a y axis.

Figure 7:
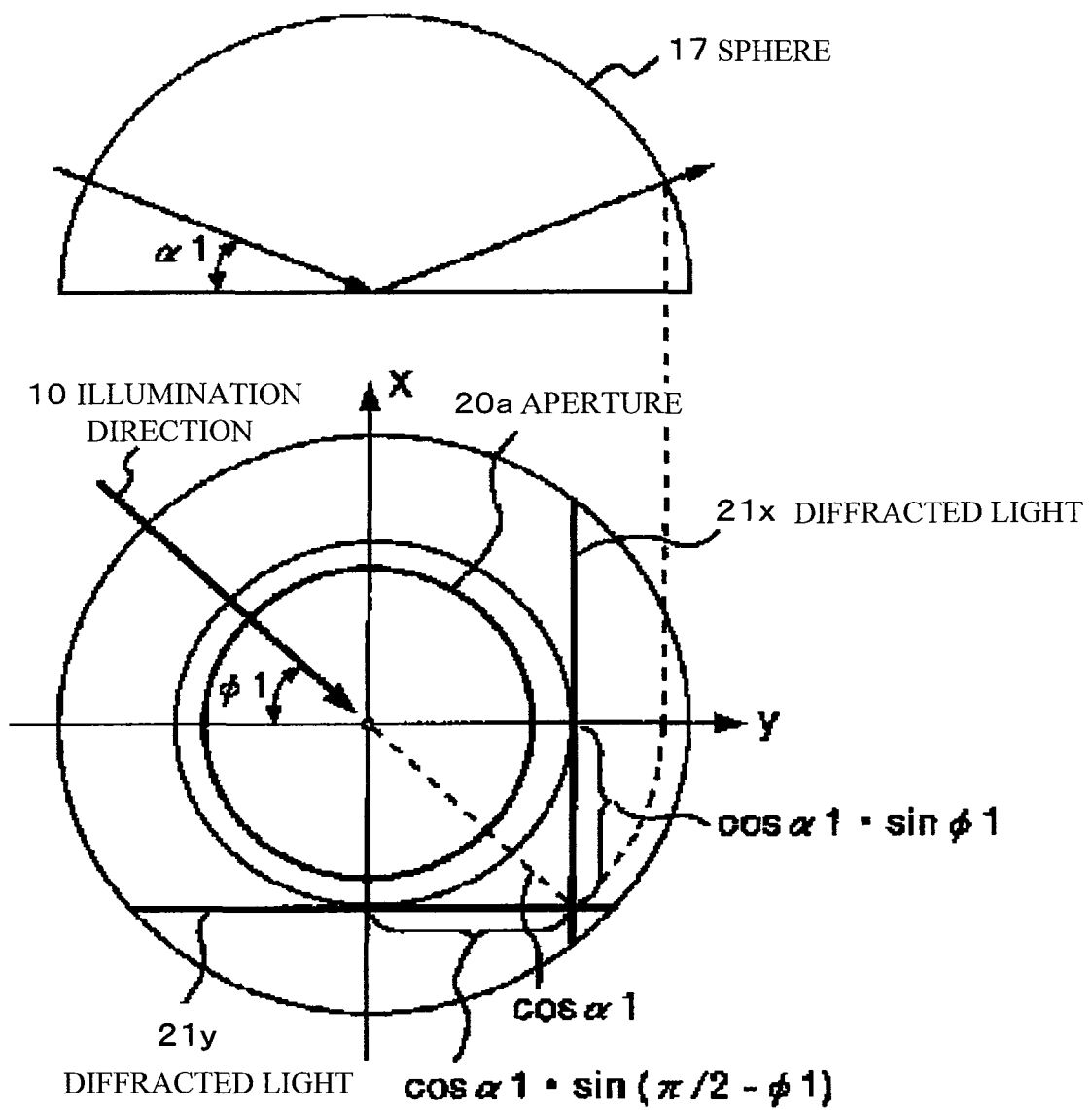
FIG. 7 is a view illustrating a relationship between an illumination direction and diffracted light.

By the way, when the detection optical system section 200 with $\beta1=0$ is not inclined, an aperture of a detection lens 201 is an aperture 20a shown in FIG. 7. Here, an upper view and a lower view in FIG. 7 are a vertical sectional view including the illumination direction 10 and a plane view, respectively. Here, an angle $\phi1$ formed by the illumination direction 10 and the y axis is set to about 45 degrees, and an angle $\phi2$ of the illumination direction 12 is also set to 45 degrees although not shown. In a case where the optical axis of the detection optical system section 200 is made perpendicular to the surface of the wafer 1, that is, $\beta1=0$, a relationship between the number of numerical aperture (NA) of the detection lens 201 and an angle $\alpha1$ of illumination light (FIG. 3) may be set according to a condition that zero order diffracted light $21x$ and $21y$ in the x and y directions from the circuit pattern where the main group of lines are directed in the x and y directions is prevented from entering an pupil of the detection lens 201.

The above condition is effective for, particularly, the inspecting object 1 including the peripheral circuit area 1ac having a non-repetition pattern in the chip 1aa as the memory LSI, the CPU core section area 1bd having a non-repetition pattern in the chip 1ba as an LSI such as a micro computer and the input/output section area 1be, and a logic LSI having a non-repetition pattern. In many cases, these LSI patterns are formed perpendicularly parallel to each other, and therefore these zero order diffracted light are emitted in a specific direction. Accordingly, the zero order diffracted light is prevented from entering the detection lens 201, thereby diffracted light from these many patterns is erased, facilitating detection of only reflected and diffracted light from the defect such as the foreign material. More specifically, the detection signal level from the circuit pattern is reduced, resulting in an increase in an area where the defect such as the foreign material can be detected with high sensitivity.

As a matter of course, in a case of the non-repetition pattern, diffracted light which is not zero order but higher order (primary, secondary, tertiary, . . . ) enters the aperture 20a of the detection lens 201, so that the higher order diffracted light appears as a group of lines parallel to zero order diffracted light $21x$ and $21y$ shown in FIG. 7. Accordingly, such higher order diffracted light is shielded by the band-like spatial filter 202 (see FIG. 3), thereby making it possible to erase the light. Note that the detection lens 201 is shown by the aperture 20a in FIG. 7. It is assumed that when an angle between a projection line to the inspecting object 1 in the illumination direction 10 and the y axis is $\phi1$, an intensity ratio of diffracted light $21x$ is cos $\alpha1\times$sin $\phi1$ and an intensity ratio of diffracted light $21y$ is cos $\alpha1\times$sin $(\pi/2-\phi1)$.

Moreover, it is needed to inspect the inspecting object 1 (wafer) for a foreign material entered a concave portion between wirings or defect and an etching remainder and the like. In such inspection (in order to prevent the zero order diffracted light from the non-repetition pattern existing in the inspecting object 1 from entering the detection lens 201), the inspecting object 1 may be irradiated from the illumination directions 10 and 12 with the slit beam 3 having a longitudinal direction of the x direction, the illumination directions 10 and 12 inclined to the y axis substantially at 45 degrees. However, when the inspecting object 1 is irradiated with such slit beam 3, it is difficult to sufficiently extract scattered light from the foreign material in the concave portion between wirings or defect between wirings or defect under a certain polarization condition of illumination light.

Accordingly, since the wiring patterns are often formed in the perpendicular direction and in the parallel direction, the inspecting object 1 is irradiated with the slit beam 3 from the illumination direction 11 parallel to the y axis by using a specific polarization condition, thereby making it possible to extract scattered light from the foreign material entered the concave portion between wirings or defect. Particularly, the wiring pattern for the memory LSI is often a linear pattern with a length of several mm in many cases, and therefore inspection with illumination from the illumination direction 11 can be performed. Furthermore, in a case of the pattern in 90-degree direction, inspection can be performed by rotating the inspecting object 1 at 90 degrees or setting the illumination direction to the x direction.

However, when the slit beam 3 is used to illuminate from the illumination direction 11, zero order diffracted light $21y'$ in the y direction in zero order diffracted light $21x'$ and $21y'$ (not shown) enters the aperture 20a of the detection lens 201, and therefore the need arises to shield and erase at least this zero order diffracted light $21y'$ by the spatial filter 202. In this case, it is, of course, possible to shield and erase higher order diffracted light by the spatial filter 202.

As mentioned above, explanation has been given of the method for erasing, particularly, the zero order diffracted light from the non-repetition pattern existing in the chip 2 of the inspecting object 1. However, in the chip 2, the repetition pattern exists as in the memory cell area 1ab in the memory LSI1aa, the register area 1bb in the LSI1ba such as a micro computer and the memory section area 1bc. For this reason, it is required to shield diffracted light fringes (diffracted interference light fringes) from the repetition pattern by the spatial filter 202.

In sum, the repetition pattern, non-repetition pattern, and no pattern are mixed in the chip 2, and line widths in the patterns are different from one another. Accordingly, in general, the shield pattern of the spatial filter 202 is set in such a way to erase diffracted light from, for example, the repetition pattern with a high frequency. Moreover, if the spatial filter 202 that can change the shield pattern as described in JP-A Nos. Hei 5-218163 and Hei 6-258239 is used, the shield pattern may be changed according to the circuit pattern in the chip 2. Furthermore, the spatial filter 202 having a different shield pattern is prepared, and then the shield pattern may be switched according to the circuit pattern in the chip 2.

An illumination polarization state may be set such that a polarization state appropriate for defect detection can be selected from various types of polarization states such as p polarization, s polarization, elliptical polarization including circular polarization, random polarization, partial random polarization and the like by combinations of polarization elements such as a polarizing plate, a wave plate, depolarizer and the like.

An explanation will be next given of detection sensitivity adjustment according to a size in defect such as a foreign material to be detected. More specifically, when a detected pixel size of the one-dimensional detectors 205 and 206 such as TDI sensor (image sensor) on the inspecting object 1 is reduced, an improvement in detection sensitivity can be expected while throughput is decreased. Alternately, detection optical system section 200 that reduces the pixel size may be used when detecting the defect such as a foreign material with a size of on the order of 0.1 µm or less. More specifically, regarding the pixel of the TDI sensor and the like, there may be provided three types of detection optical system sections 200 capable of obtaining three image sizes of 2 microns, 1 micron and 0.5 micron on the inspecting object 1.

In a method for implementing the aforementioned configuration: all detection optical system section 200 may be switched to another one; only the imaging lens 203 may be switched to another one; or the detection lens 201 may be switched to another one. In this case, the configuration of lens may be designed so as not to change an optical path length from the laser beam source 101 to the one-dimensional detectors 205 and 206 such as the TDI sensor and the like. In a case where such design is difficult to be achieved, a mechanism that can change the distance up to the one-dimensional detectors 205 and 206 may be, of course, when switching the lens. Furthermore, the one-dimensional detectors 205 and 206 whose pixel sizes in themselves are changed.

An explanation will be next given of a specific embodiment of a relationship between slit beams 3 from three directions and the one-dimensional detectors 205 and 206.

As shown in FIG. 4, in a case where multiple illumination beams divided and obtained from the same laser beam source 101 is emitted from the illumination directions 10 and 12, overlapping of these beams will cause variations in intensity in an illumination range due to interference. Accordingly, illumination is performed in such a way to prevent overlapping of these slit beams 3 in the range of the detection area 4 (see FIG. 5) to thereby make it possible to remove an adverse influence of interference. In a case of using the TDI sensor as the one-dimensional detectors 205 and 206, detected outputs are integrated in the y direction in synchronization with running of the y stage, so that there is no problem if the position is shifted in this way. Similarly, in a case of using the slit beams 3 from the illumination direction 11, illumination may be performed after three beams are arranged in such a way that overlapping of these beams causes no problem. It is needless to say that the same holds true in a case where two beams among the illumination directions 10, 11, 12 are used.

Moreover, although not illustrated here, if the slit beams 3 from the illumination directions 10 and 12 are simultaneously radiated onto with the same location to overlap with each other, interference occurs. Even in this case, interference fringes, however, are inclined in the y direction, so that variations in intensity of illumination due to interference can be reduced by an integration effect of the one-dimensional detectors 205 and 206. For this reason, there is no need to prevent overlapping of the beam from the illumination direction 10 and the beam from the illumination direction 12 when illumination is performed.

An explanation will be next given of a mode for further increasing the number of illumination incident directions. Although the example in which illumination from three directions is shown in FIGS. 4 and 5, this example has difficulty in increasing the capture rate of the foreign material, which is larger than a fraction of an illumination wavelength, and depression and groove shape defects on the inspecting object 1. This is because scattered light from these defects has a tendency to show high directivity, and also because scattered light enters or does not enter a converging angle of the detection optical system due to asymmetry of the defect shape.

Figure 8:
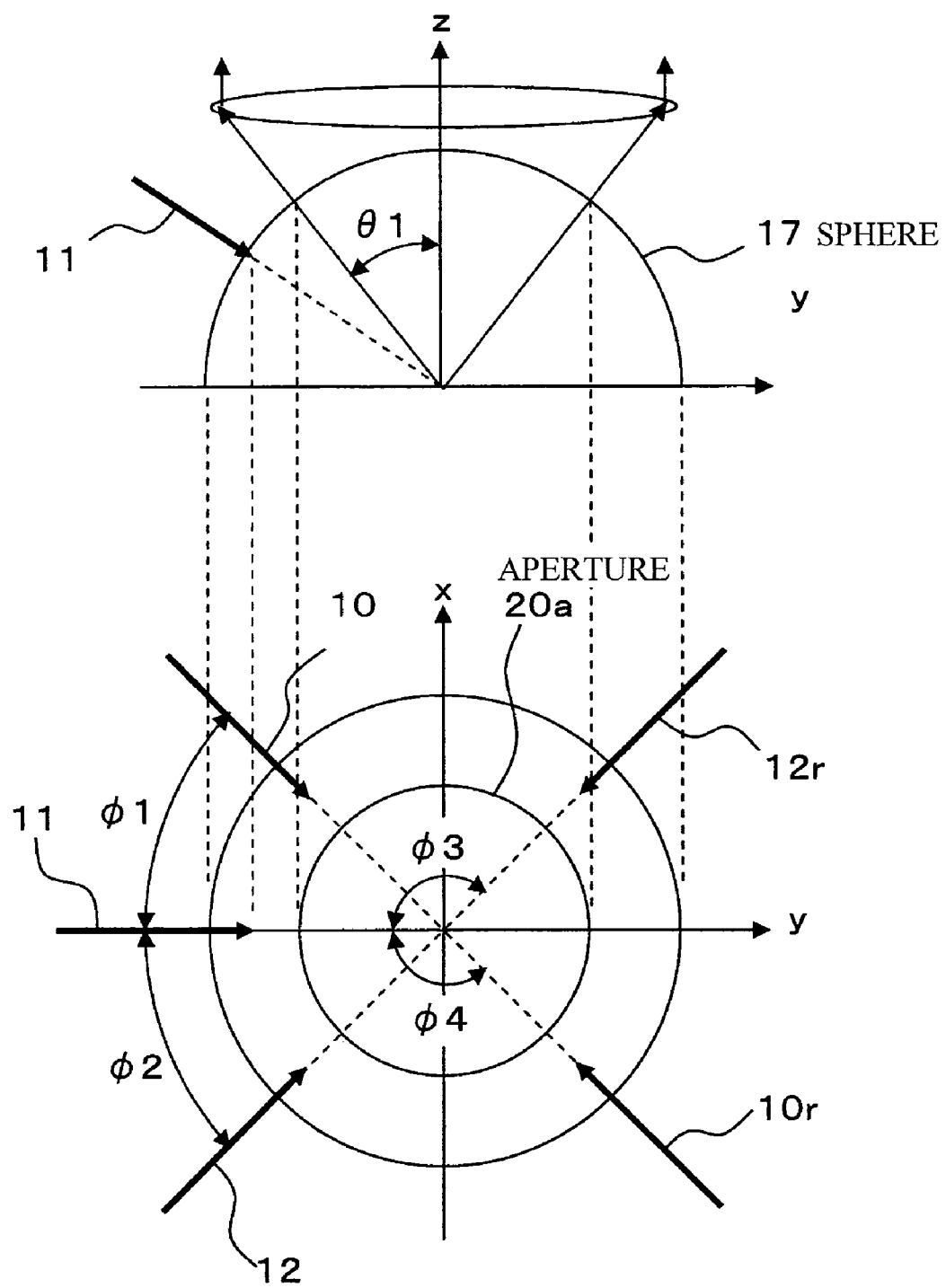
FIG. 8 is a view illustrating a relationship between incident light and an aperture of a detection lens when a surface of an inspecting object is irradiated with slit beams from five directions.
Figure 9:
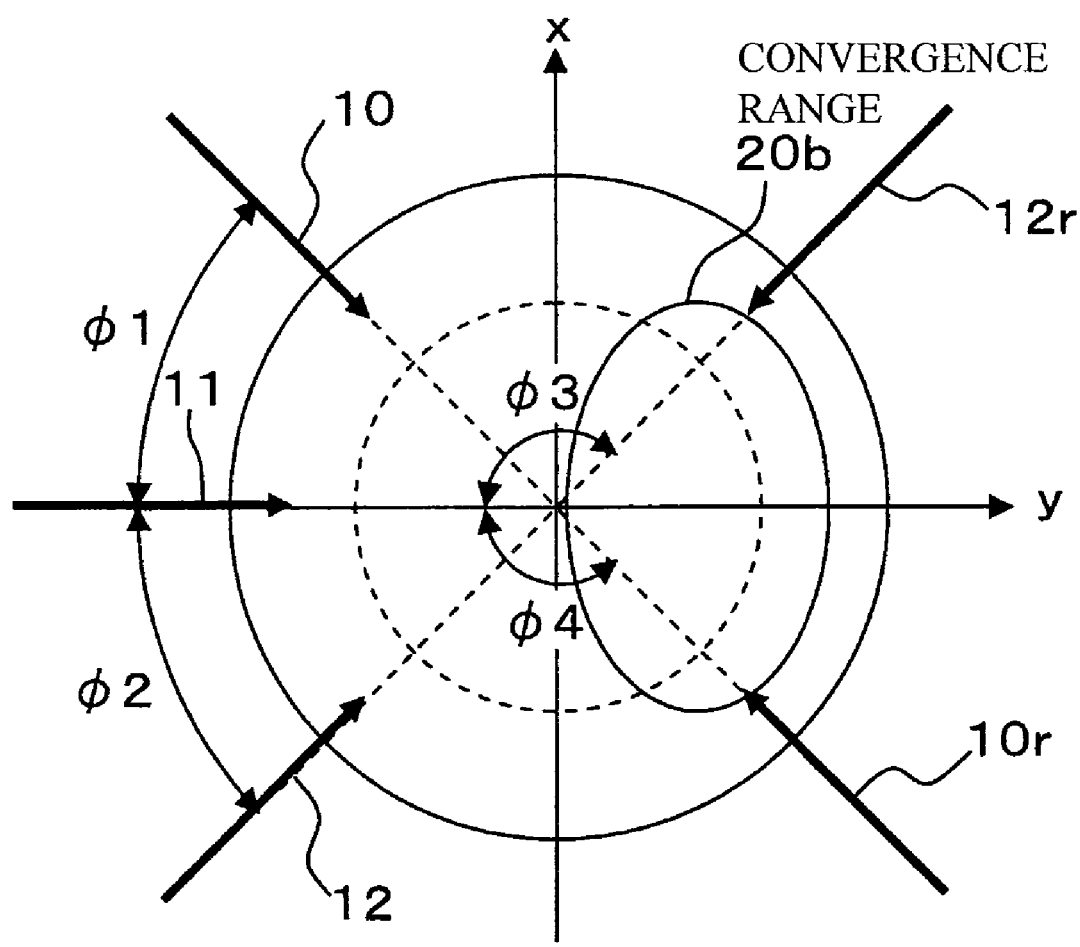
FIG. 9 is a view illustrating a relationship of an aperture of an inclined detection light lens when an inspecting object is irradiated with slit beams from five directions.

In order to enhance the capture rate of such defects, the number of illumination incident directions may be increased. For example, as shown in FIG. 8, illumination light beams are additionally made incident from illumination directions 10r and 12r, which are opposite to the illumination directions 10 and 12, respectively, so that the illumination beams from the four directions enter symmetrically. Here, an upper view is a vertical sectional view including the illumination direction 11 and a lower view is a plane view. Moreover, an angle between the illumination direction 11 and the illumination direction 12r is $\phi 3$, and an angle between the illumination direction 11 and the illumination direction 10r is $\phi 4$. Note that the angle between the illumination direction 11 and the illumination direction 10 is $\phi 1$, and that the angle between the illumination direction 11 and the illumination direction 12 is $\phi 2$, as mentioned previously. This makes it possible to cancel out the influence of asymmetry of the defect shape. Moreover, in a case where an optical system to be described later in which the optical axis of the detection optical system section 200 is inclined at $\beta 1$ from a vertical direction, a convergence range of the detection lens 201b (FIG. 10) is placed in such a way to be shifted from the illumination position as shown by 20b in FIG. 9 or 20c in FIG. 10, thereby forward-scattered light from the illumination directions 10 and 12 and backward-scattered light from the illumination directions 10r and 12r are detected by the detection lens 201b, allowing further detection of defects each having a different scattering direction and distribution.

An explanation will be next given of a case where the optical axis of the detection optical system section 200 is inclined at $\beta 1$ ($\neq 0$) from a vertical direction. The inclination allows more scattered light to be introduced into the detection optical system from particles (foreign materials) to be detected, thereby enhancing intensity of scattered light from the defects such as foreign materials to improve detection sensitivity.

This is because scattered light from the particle is larger at the forward portion than scattered light from surface roughness and the like. More specifically, the particle (foreign material) causes larger light beams to be scattered in forward directions since the size of the particle is larger than a fraction of an illumination wavelength, while the surface roughness causes light beams to be substantially isotropically scattered since the size of the surface roughness is close to $\frac{1}{10}$ or less of the wavelength. As a result, even if multiple roughness portions on the surface of the circuit pattern exist in the detected pixel, the distribution of the roughness portions is substantially isotropic. Accordingly, use of forward scattered light makes it possible to detect particles or defects with a high SN ratio relative to the surface roughness. However, when the TDI sensor is used, the optical axis of the detection optical system section 200 cannot be inclined because of the relationship of the depth of focus. For this reason, when $\beta 1 = 0$ is not established, it is effective to use the one-dimensional sensor.

Figure 10:
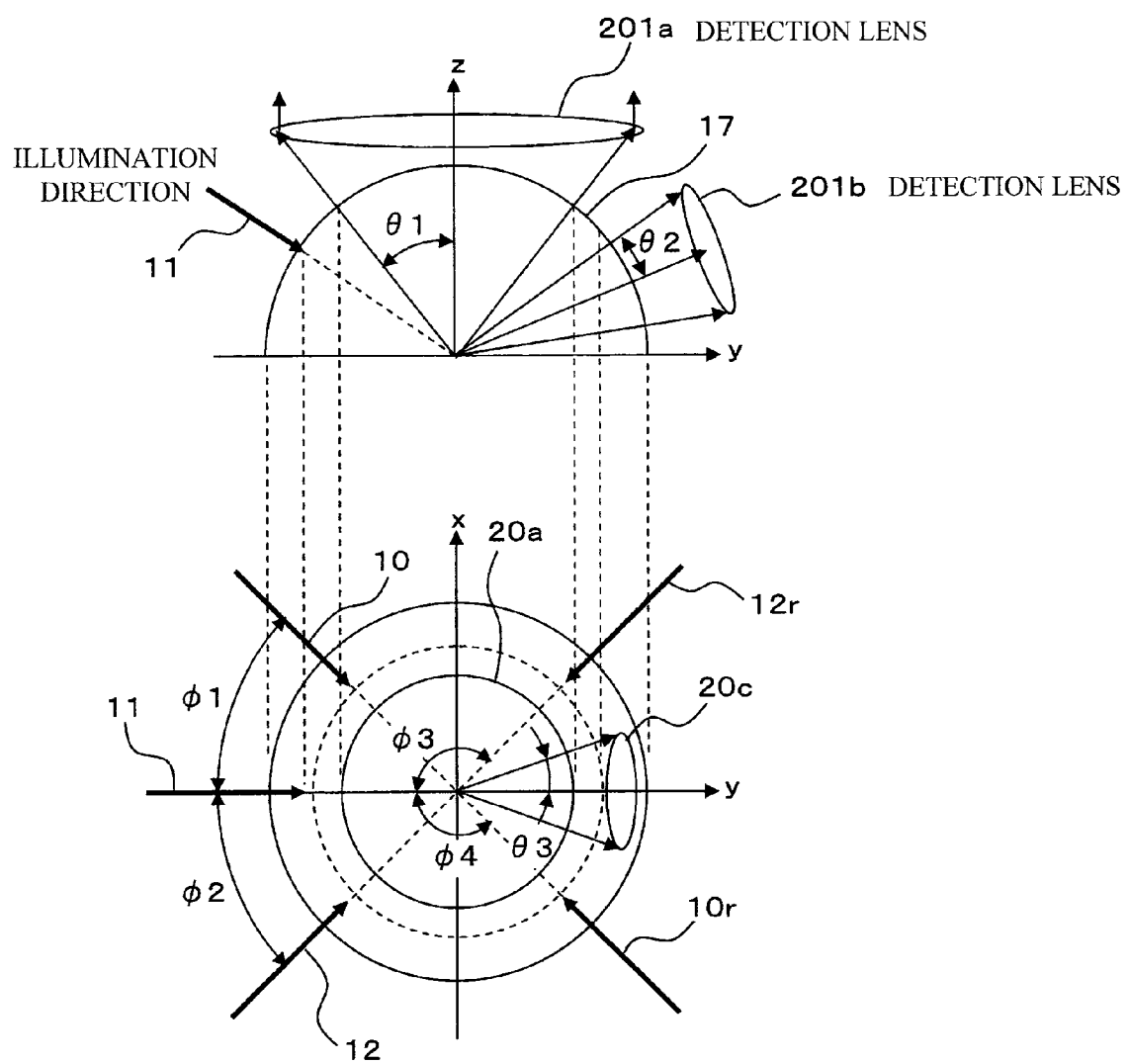
FIG. 10 is a view illustrating a relationship of apertures of two detection lens when an inspecting object is irradiated with slit beams from five directions.

An explanation will be next given of a case where both the optical system where the optical axis of the detection optical system section 200 is placed in the normal direction of the inspecting object 1, that is, an inclined angle of the optical axis is $\beta 1 = 0$, and the optical system where the optical axis of the detection optical system section 200 is inclined at $\beta 1$ ($\neq 0$)

from the normal direction. FIG. 10 shows an example of arrangement of converging angles of the lenses 201 of the detection optical section when two optical systems are used. It is assumed that the detection lens 201 of the optical system where the inclined angle of the optical axis is β1=0 is a detection lens 201a, and that the detection lens 201 of the optical system where the optical axis of the detection optical system section 200 is inclined at φ1 (≠0) from a vertical direction is a detection lens 201b. It is also assumed that a converging angle of the detection lens 201a in a direction of an elevation angle is θ1, that a converging angle of the detection lens 201b in a direction of an elevation angle is ƒ2, and that a converging angle of the detection lens 201b in a direction of an azimuth angle is θ3.

Among the defects such as the foreign material, in a case where the defect whose size is close to ⅒ or less of the wavelength, scattered light is substantially isotropically scattered, and therefore detection may be performed by the optical system where the inclined angle of the optical axis is β1=0. However, since an amount of scattered light is proportional to the fifth power of the size of the defect, the scattered light intensity becomes extremely weak, and therefore the converging angle θ1 of the detection lens 201a may be set to, for example, 37 degrees or more to cover 20% or more of the entire solid angle. At this time, a range of θ2 that can be set is 26.5 degrees or less, making it impossible to increase the converging angle. In such a case, the converging angle θ3 in the direction of the azimuth angle may be set to be larger than θ2. For example, assume a following case: θ1 is 37 degrees; θ2 is 8 degrees; and β1=68 degrees. In such case, θ3 is set to about 27 degrees, thereby making it possible to ensure about 5% of the entire solid angle as a collection solid angle. As a result, it is possible to detect both the defect which is ⅒ or less of the wavelength, and the particle (foreign material) which is larger than a fraction of the illumination wavelength, with high sensitivity.

Figure 11:
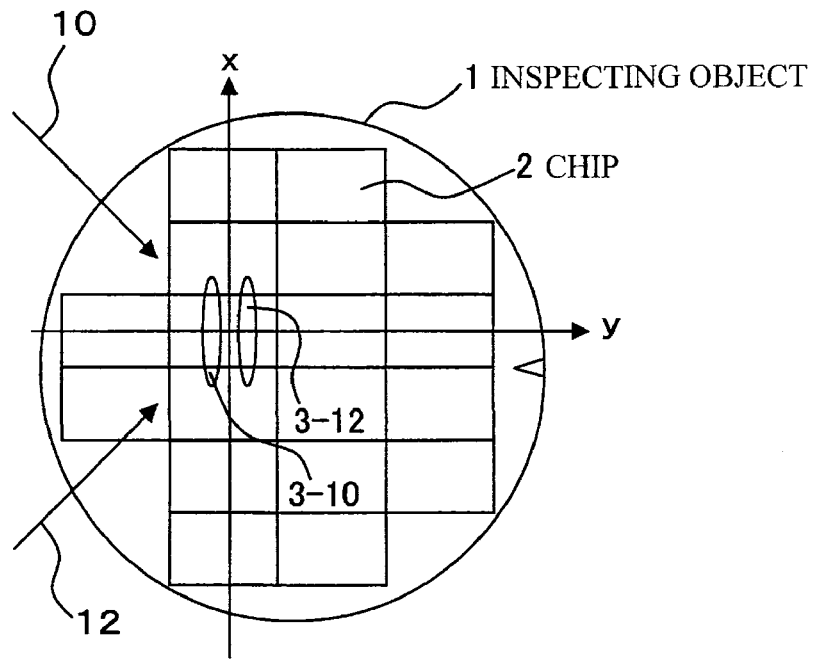
FIGS. 11A and 11B are views each illustrating a relationship between an illumination direction and an irradiation position when two beams in different illumination directions are applied to different positions on an inspecting object.
Figure 11:
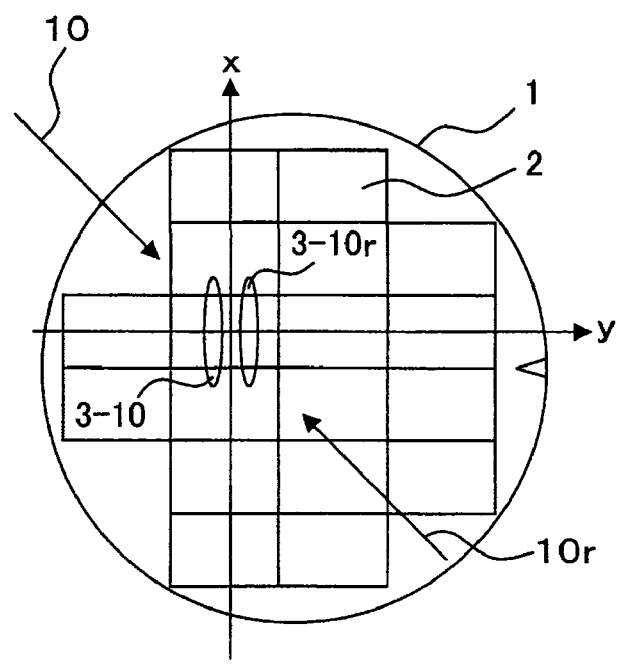
Figure 12:
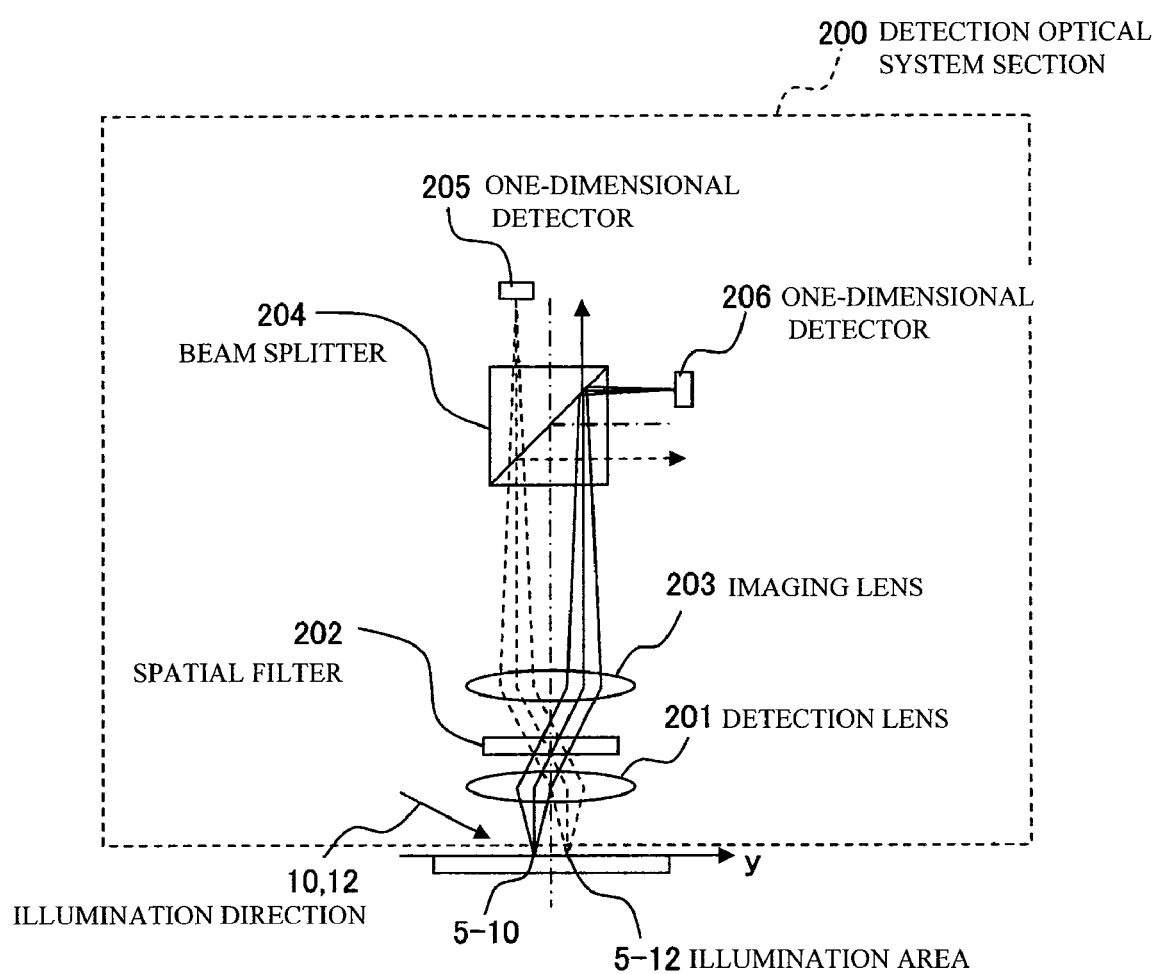
FIG. 12 is a view illustrating a relationship between an illumination direction and a sensor position when two beams in different illumination directions are applied to different positions on an inspecting object.

An explanation will be next give of classification of defects by using the one-dimensional detectors 205 and 206. As illustrated in FIG. 11A, by using both light from the illumination direction 10 and light from the illumination direction 12, an irradiation range 3-10 irradiated with light from the illumination direction 10, and an irradiation range 3-12 irradiated with light from the irradiation direction 12, are placed so as to be different positions on the surface of the surface 1. As illustrated in FIG. 12, two illumination regions 5-10 and 5-12 are detected by two one-dimensional detectors 205 and 206, respectively. More specifically, two detectors are arranged such that the one-dimensional detector 205 detects transmitted light of the beam splitter 204, and that the one-dimensional detector 206 detects reflected light of the beam splitter 204 to thereby detect scattered light independently under two different types of illumination conditions.

Moreover, by giving a difference in incident angle, a difference in polarization state and a difference in wavelength in addition to the difference in azimuth angle of illumination, it is possible to detect defects having different characteristics and types and to achieve improvement in sensitivity by increasing the number of types of detecting defects. Furthermore, by making a comparison of coordinates or scattered light intensity between the defect detected by the one-dimensional detector 205 and the defect detected by the one-dimensional detector 206, it is possible to classify detected defects. In addition, removal of a defect which requires no detection, and a cause of defect occurrence, and an apparatus which is a source of defect occurrence, can be found out according to an increase and decrease in a defect having a specific characteristic, and which enables to minimize a reduction in yield due to prompt measures. Moreover, as shown in FIG. 11B, by using both light from the illumination direction 10 and light from the illumination direction 10r makes it possible to regard asymmetry of the defect shape as a characteristic and classify the defect.

Figure 13:
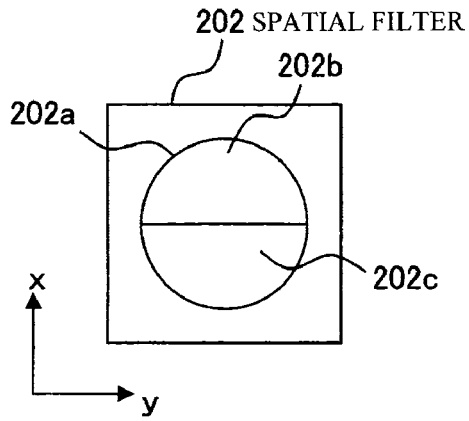
FIGS. 13A to 13E are views each illustrating an example of a spatial filter to be used when two beams in different illumination directions are applied to different positions on an inspecting object.
Figure 13:
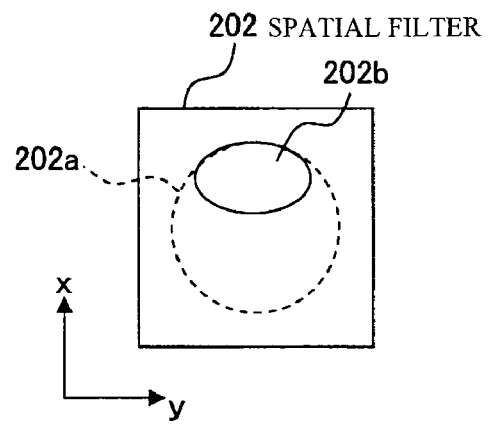
Figure 13:
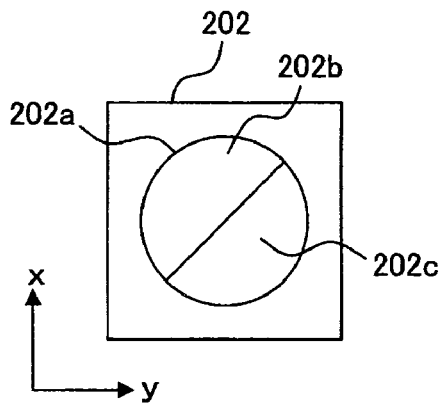
Figure 13:
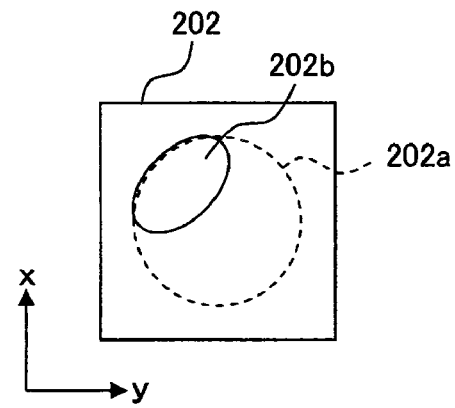
Figure 13:
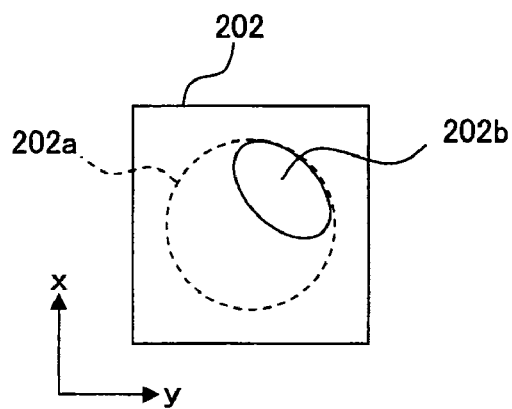

Furthermore, a filter shown in FIG. 13 is used as the spatial filter 202 in FIG. 12 in addition to the filter that shields diffracted light from the repetition pattern on the surface of the inspecting object 1, thereby allowing classification between a defect having strong forward scatter and a defect having strong backward scatter.

First, description will be given of a case where illumination shown in FIG. 11A and the spatial filters shown in FIGS. 13A and 13B are used. In the spatial filter 202 shown in FIG. 13A, light passes through only a portion 202b in an area 202a of the spatial filter surface on which light enters while a portion 202c is shielded. Moreover, in the spatial filter 202 in FIG. 13B, light passes through only a portion 202b in an area 202a of the spatial filter surface on which light enters while the rest of the portion is shielded.

As shown in FIG. 11A, when the inspecting object 1 is irradiated with light from the illumination direction 10 and the illumination direction 12, the light scattered substantially forward by illumination from the illumination direction 10 reaches in the vicinity of the portion 202c on the spatial filter surface, and therefore is shielded and does not arrive at the one-dimensional detector 206. On the other hand, light scattered substantially backward by illumination from the illumination direction 10 reaches in the vicinity of the portion 202b on the spatial filter surface, and therefore arrives at the one-dimensional detector 206 to be detected. Similarly, regarding light from the illumination direction 12, light scattered substantially forward reaches in the vicinity of the portion 202b on the spatial filter surface, and therefore arrives at the one-dimensional detector 205 to be detected. By making a comparison of an amount of characteristic of defect such as coordinates and scattered light intensity between a defect detected from a detection signal by the one-dimensional detector 205 and a defect detected from a detection signal by the one-dimensional detector 206, it is possible to classify the defects. Furthermore, the same classification as mentioned above can be expected if illumination shown in FIG. 11B and the spatial filter shown in FIG. 13C or 13D are used.

Moreover, using illumination shown in FIG. 11B and the spatial filter shown in FIG. 13E allows classification according to deviation of side-way scattering. Furthermore, the use of only light of the specific area on the spatial filter as shown in FIG. 13 for defect detection allows to shield scattered light from the repetition pattern on the wafer and the detection which requires no defection, and to selectively detect a defect which is important for managing yield.

Figure 14:
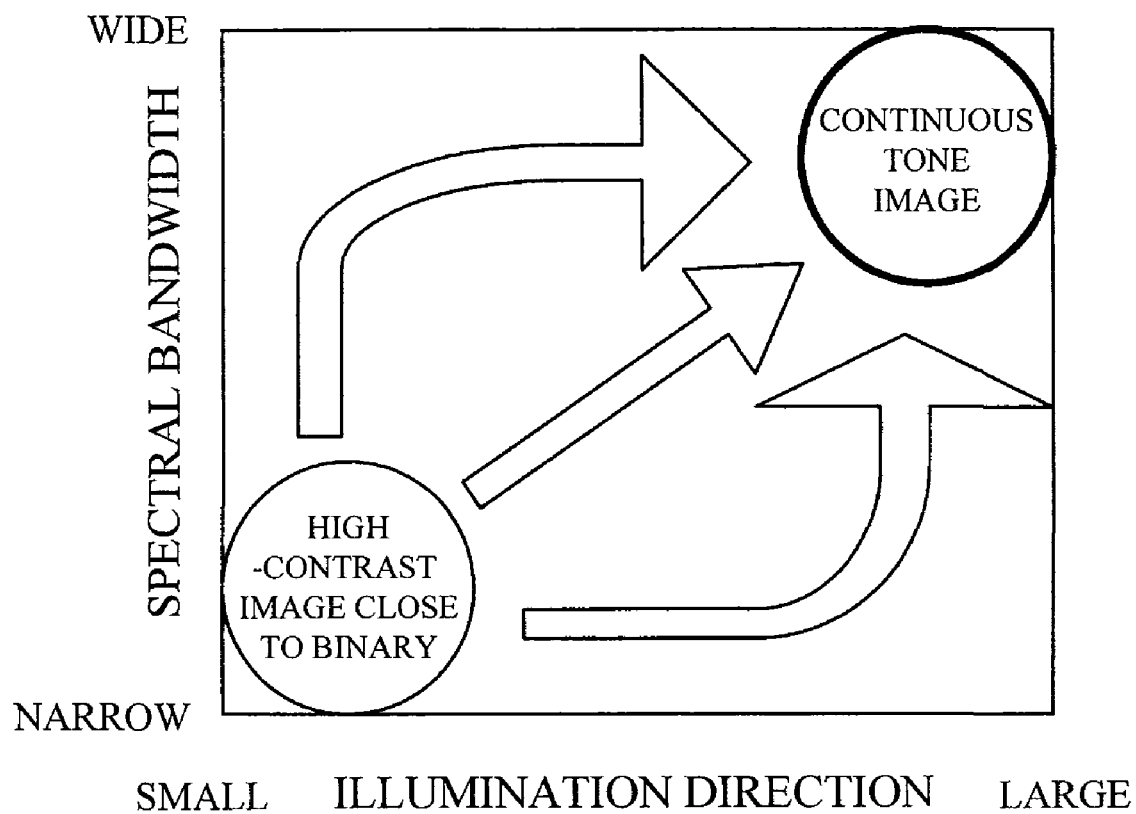
FIG. 14 is a view conceptually illustrating an effect that a bandwidth of an illumination wavelength and the number of illumination directions have on a grayscale characteristic of an image.
Figure 15:
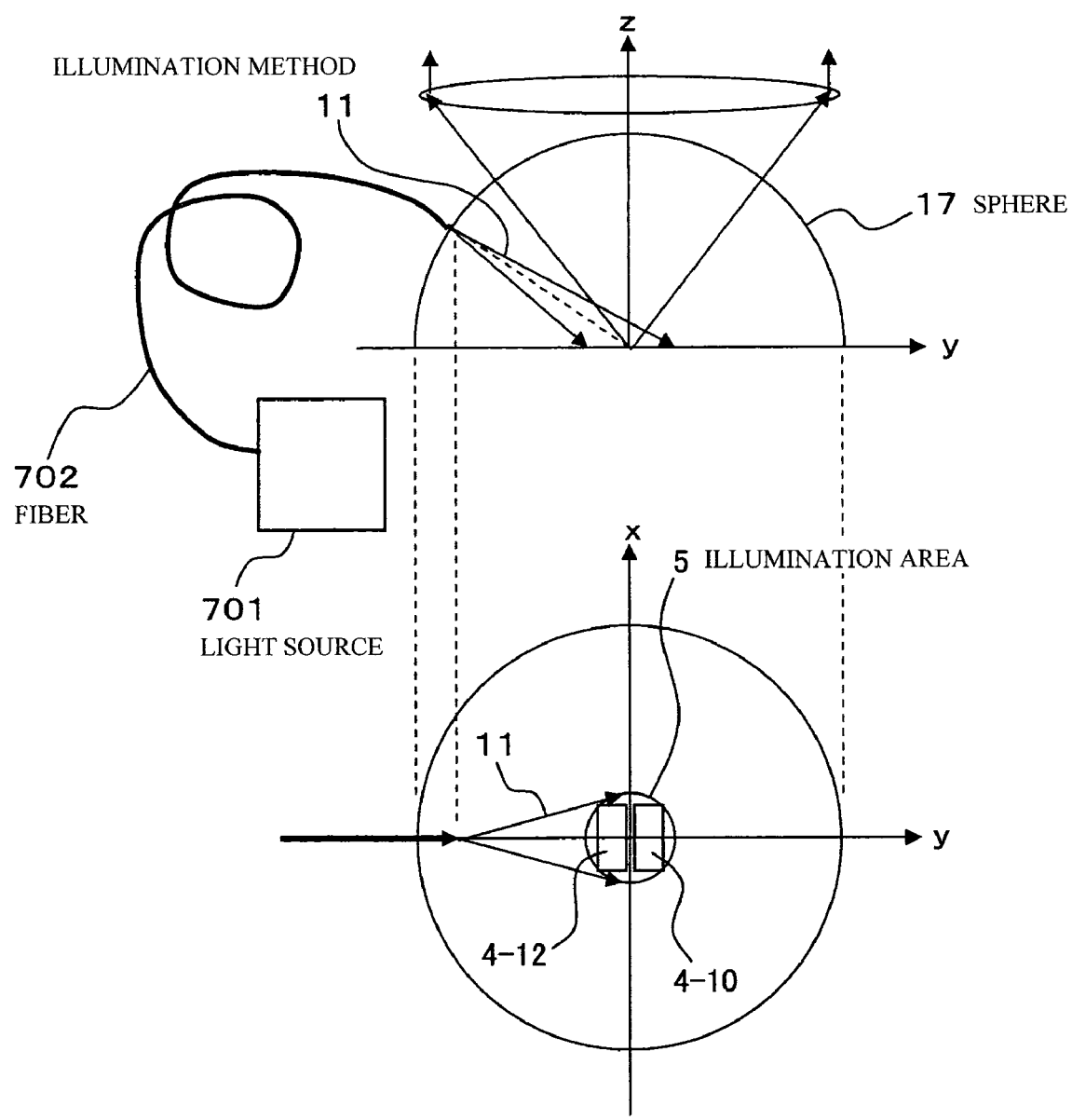
FIG. 15 is a view illustrating a relationship between an illumination area to be illuminated by using an optical fiber and detection areas.

In addition, as illustrated in FIG. 14, it is also possible to bring a high-contrast image, which is close to a binary image, to a more continuous tone image by increasing the number of illumination directions with use of a light source for a single wavelength light such as a laser. This provides improvement, particularly, of the defect detection characteristic of the non-repetition pattern on the wafer. Multi-directional illumination may be performed by guiding illumination light beams in individual illumination directions, that is, output light from a light source 701 into an optical fiber 702 as shown in FIG. 15. This makes it possible to largely simplify the illumination optical system and provide multi-directional illumination from five or more directions at low cost. When the optical fiber is used for illumination, an optical system may be attached to the top end of the optical fiber to provide slit-like illumination, but the inspecting object 1 may be directly irradiated with light emitted from the end of the optical fiber in order to simplify the illumination system.

In a case where no additional optical system is provided at the output end of the fiber, an illumination area 5 expands. However, in a case where a high sensitivity TDI sensor with on the order of 4000 pixels and 1000 TDI stages is used, aspect ratio of total detection area including the areas 4-10 and 4-12 is reduced, and therefore illumination efficiency is not much lost. Note that, in addition to guiding light having an illumination wavelength with the optical fiber, light of pumping laser or that of fundamental laser may be guided in the vicinity of the inspecting object 1 with the optical fiber and wavelength-converted to an illumination wavelength with a wavelength conversion head attached to the top end of the optical fiber. Moreover, when performing multi-direction illumination, output light from one laser beam source 701 may be divided and guided with the optical fiber instead of preparing the number of beam sources 701 corresponding to the number of illumination directions.

(Data Processing Section)

The data processing section 400 in FIG. 3 performs data processing (image processing) on output signals from the one-dimensional detectors 205 and 206 and displays a processing result on an output section 417. Moreover, the data processing section 400 controls ON/OFF of the output from the laser beam source 101 and varies a wavelength as required. Furthermore, the output section 417 outputs (displays) a stage position by using a signal of the stage controller 305.

Figure 16:
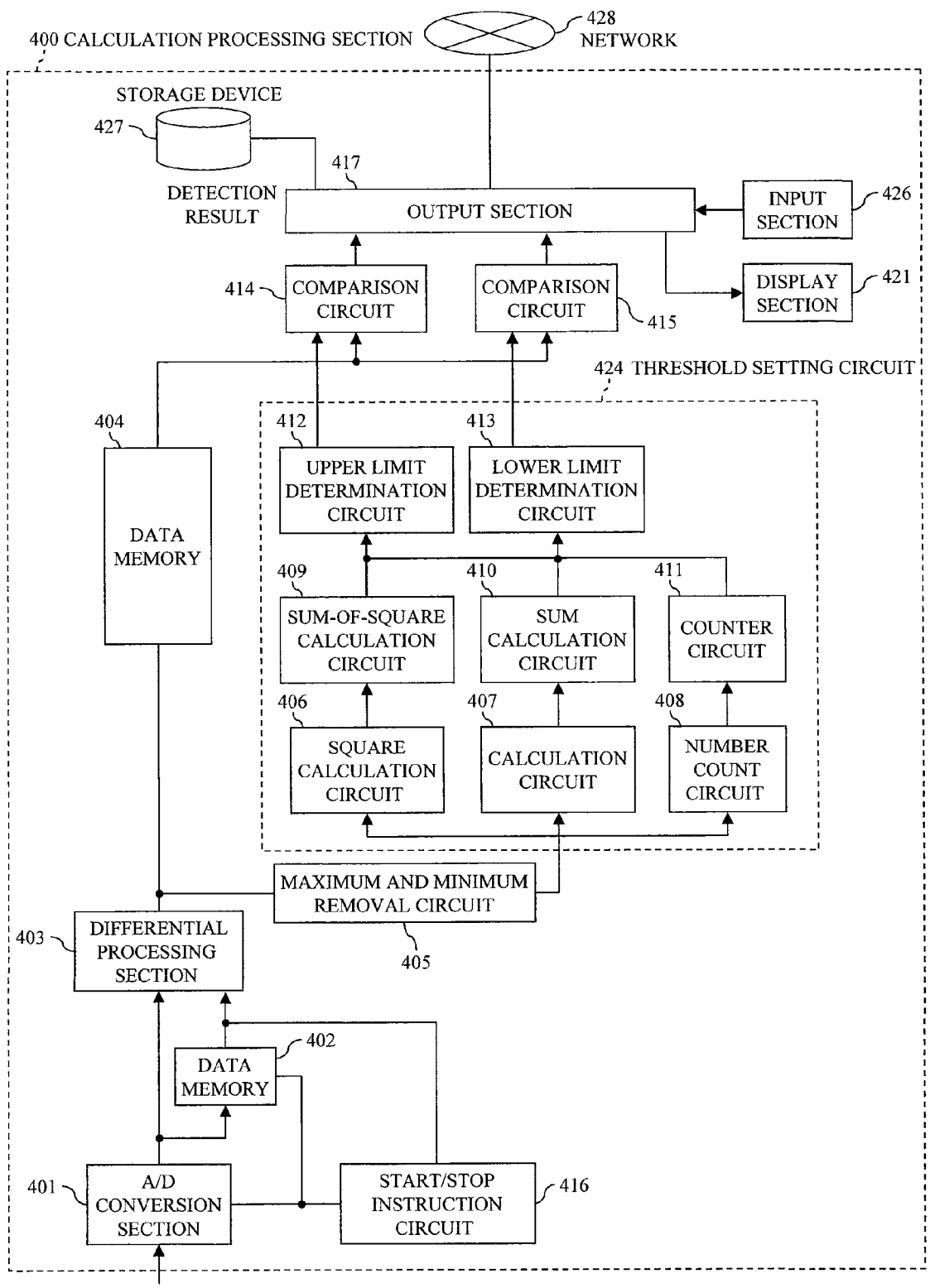
FIG. 16 is a configuration view of a data processing section.

FIG. 16 is a detailed configuration diagram of the data processing section 400. The data processing section 400 includes: an A/D conversion section 401 that inputs a repetition signal by which a signal corresponding to one chip is repeated, and that converts an analog image signal to a digital image signal; a data memory 402 that stores the signal corresponding to one chip, and that outputs a delay signal corresponding to one chip; a start/stop instruction circuit 416 that takes sampling timings; a differential processing section 403 that calculates a differential signal between an output signal of the A/D conversion section 401 and an output signal of the data memory 402; a data memory 404 that temporarily stores the differential signal; a maximum and minimum removal circuit 405 that removes the maximum and the minimum abnormal signals found in the differential signals; a threshold setting circuit 424; a comparison circuit 414 that compares a positive-side threshold set in the threshold setting circuit 242 with a signal primarily stored in the data memory 404 to output a signal indicating a defect such as a foreign material; a comparison circuit 415 that compares a negative-side threshold set in the threshold setting circuit 424 with a signal primarily stored in the data memory 404 to output a signal indicating a defect such as a foreign material; a storage device 427; a display section 421; an input section 426; and an output section 417 that adds position coordinates in a coordinate system set relative to the inspecting object 1 to a signal indicating a defect such as a foreign material to be output from each of the comparison circuits 414 and 415, and that further outputs a detection result including information on the inspecting object 1. The output of the output section 417 is connected to a network 428.

Furthermore, the threshold setting circuit 424 includes: a square calculation circuit 406 that calculates squares of signal level s; a calculation circuit 407 that calculates signal level s; a number count circuit 408; a sum-of-square calculation circuit 409 that integrates squares of signal level s; a sum calculation circuit 410 that integrates signal level s to calculate a sum; a counter circuit 411 that calculates the number of samplings n for obtaining a variation; an upper limit determination circuit 412; and a lower limit determination circuit 413.

It should be noted that the maximum and minimum removal circuit 405 is not always needed. In a case where the maximum and minimum removal circuit 405 is not used, all image data (including image data showing the foreign material) to be detected when calculating the level of the threshold will be used, and therefore it is possible to correctly and stably detect the level of the threshold. On the other hand, the threshold thus prepared cannot be used for inspecting the foreign material which exists in the area based on which the threshold is prepared. Accordingly, a threshold of which area is to be desirably inspected must be prepared in an area corresponding to another chip array of the inspecting object 1. As a result, the need arises to perform threshold preparation and foreign material inspection in different lines, resulting in that somewhat greater throughput is required. Particularly, when the number of chips is small, a threshold may be prepared by using image data over multiple lines. In this case, a data capturing position is designated by the start/stop instruction circuit 416.

Moreover, the output section 417 is provided with a CPU that controls the entire defect inspection apparatus 1000 for inspecting the defect such as the foreign material according to the present embodiment. In addition, the circuits 406 to 411 are used to obtain a variation (standard deviation) σ of a background signal at every predetermined area in the chip. Then, the upper limit determination circuit 412 and the lower limit determination circuit 413 set positive-side and negative-side thresholds Th (H) and Th (L) for extracting a signal which indicates a defect such as a foreign material, in response to the obtained variation σ of the background signal at every predetermined area in the chip. These circuits 406 to 413 constitute the threshold setting circuit 424. On the other hand, the data memory 404 is used for temporarily storing detected digital image signal until the threshold is set by the threshold setting circuit 424. Moreover, the position coordinates in the coordinate system set relative to the inspecting object 1 are obtained by using a reference mark provided in the inspecting object 1 as an origin, according to displacement of the stage measured by a length measuring machine (not shown) and a reading signal (scanning signal) of the TDI sensor and the like. Furthermore, the display section 421 is a display such as CRT and displays data obtained from the output section 417, for example, the positive-side threshold Th (H) indicating a variation. Providing the display section 421 makes it possible to determine whether or not the threshold is an optimal value at every area in the chip while checking the defect extraction outputs of such as foreign materials to be extracted from the comparison circuits 414 and 415.

Here, the output section 417 for outputting the detection result includes: one that prints out the result as a hard copy; one that records the result in a hard disk, a flexible disk, a magneto-optic recording medium, an optical recording medium, an LSI memory card, and the like; and a network connected to a management system which controls another inspection apparatus or inspection system, or a manufacturing process apparatus or a manufacturing line. In addition, the output section 417 is provided with a CPU that controls the entire defect inspection apparatus for inspecting the defect such as the foreign material according to the present embodiment. Here, the A/D conversion section 401 converts signals to be outputted from the one-dimensional detectors 205 and 206 to pixel signals represented by digital signals. Then, the A/D conversion section 401 may be placed in the same substrate in the data processing unit 400 or may be placed close to the one-dimensional detectors 205 and 206 such as TDI sensor in the detection optical system section 200. In a case of placing the A/D conversion section 401 close to the one-dimensional detectors 205 and 206, there is an advantage that noise is reduced at the time of transmission due to digitization, while there is a disadvantage that the number of signal transmission cables is increased.

In the device such as the LSI being an actual inspecting object 1, variations can be found on detection signals which are obtained from the one-dimensional detectors 205 and 206 because of a subtle difference in the process that is not regarded as a defect and of noise which occurs at the time of detection. In other words, as shown in FIG. 17A, corresponding pixels between chips 71 and 72, for example, signal levels of areas 73 and 74 are not identical with each other and variations occur.

More specifically, variations in the detection signals differ according to areas 75, 76, 77 (for example, in a case of the memory LSI, such as memory cell area, peripheral circuit area, and the other area) each having a different pattern structure as shown in FIG. 17B. As a result, in an area where a variation is small, it is possible to detect a small defect that causes a smaller change in the signal, while in an area where a variation is large, it is possible to detect only the large defect that causes a large change in the signal.

Accordingly, the characteristic of the data processing section 400 lies in that the variation (standard deviation) is calculated between chips corresponding at every pixel in the chip, and that the calculated value is used to set the threshold. By this means, inspection is carried out by determining the defect such as the foreign material by using the small threshold in the area where the variation is small and by using the large threshold in the area where the variation is large. This makes it possible to reduce the threshold to be used in the area where the variation is small (for example, the memory cell area such as the memory LSI) without being influenced by the area where the variation is large, resulting in the detection of a fine foreign material having a size of 0.1 µm or less.

Figure 17:
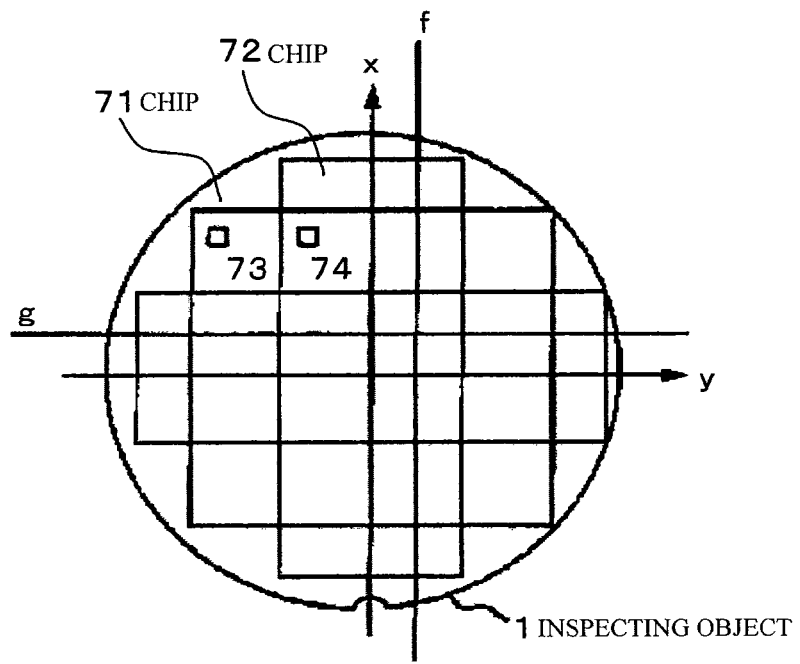
FIGS. 17A and 17B are diagrams for explaining calculation and setting of a criterion (threshold) for extracting a defect such as a foreign material.
Figure 17:
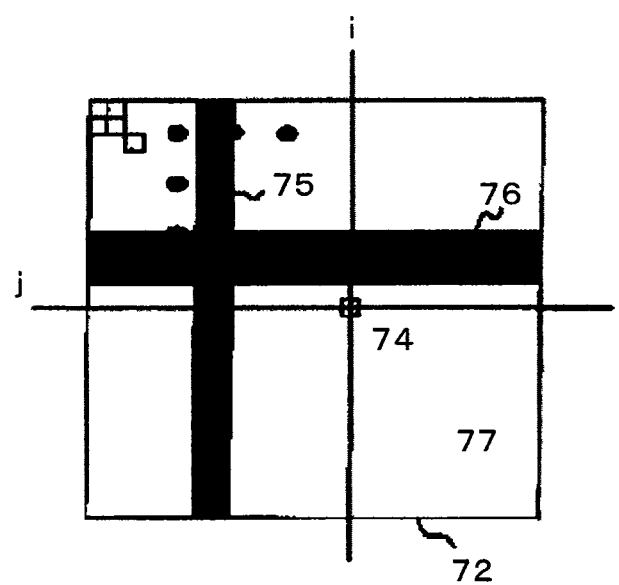

Here, an explanation will be given of the content of signal processing to be performed by the threshold setting circuit 424 with reference to FIG. 17. FIG. 17A shows an example of an array of chips 71, 72 and the like on the inspecting object 1. In many LSI manufacturing, the same types of these chips are repeatedly manufactured. In some cases, multiple chips (about two to four) are simultaneously manufactured at one exposure. In this case, the same pattern is created at the same position between these chips. Accordingly, the detection signals of the corresponding positions of these chips are originally the same. It is assumed that signals of i-th and j-th pixels (i, j) in f-th and g-th chips (f, g) are s (i, j, f, g).

However, in practice, by a subtle difference in the process that is not regarded as a defect and noise caused at the time of detection, variations occur in the detection signal s of the corresponding pixels between chips. Moreover, even in the chip, the variation differs at the area having a different pattern structure. Accordingly, variations of detection signal s (i, j, f, g) (standard deviation $\sigma$ (s, f, g) between the corresponding positions of chips are obtained according to the following equation (1) to set thresholds Th (H) and Th (L).

$$Th(H) = \mu(s,f,g) + m1 \times \sigma(s(i,j,f,g),f,g)$$

$$Th(H) = \mu(s,f,g) - m1 \times \sigma(s(i,j,f,g),f,g) \quad (1)$$

Here, the threshold Th (H) is set by the positive-side upper limit determination circuit 412 (see FIG. 16), and the threshold Th (L) is set by the negative-side upper limit determination circuit 413. It should be noted that $\mu$ (s, f, g) is a mean value obtained when values f and g of signal s to be calculated according to the following equation (2).

$$\mu(s,f,g) = \Sigma s(i,j,f,g)/n \quad (2)$$

$\Sigma$s (I, j, f, g) is calculated by the calculation circuit 407 that calculates signal level s and the integration circuit 410 that integrates the signal level s, and n is calculated by the number count circuit 408 and the counter circuit 411. Moreover, $\sigma$ (s, f, g) indicates a standard deviation obtained when values of f and g of signal s to be calculated according to the following equation (3) are changed. In addition, m1 is a magnification (coefficient).

$$\sigma(s,f,g) = \sqrt{(\Sigma s(i,j,f,g)^2/n - \Sigma s(i,j,f,g)/n} \quad (3)$$

$\Sigma$s (i, j, f, g)$^2$ is calculated by the square calculation circuit 406 that calculates squares of signal level s and the sum-of-square calculation circuit 409 that integrates squares of signal level s. In this way, the threshold is fixed to the result obtained by increasing the standard deviation $\sigma$ (s, f, g) severalfold. Moreover, it is desirable that the magnification m1 be normally on the order of 6. This is because the probability of occurrence of 6$\sigma$ or more is on the order of $1 \times 10^{-11}$. This probability is figured out based on a fact that, when the wafer having $\phi$300 mm, for example, is detected with a pixel size of 2×2 microns, the number of obtained images is about $7 \times 10^{10}$, so that a value exceeding this threshold (false alarm) is less than one pixel over the entire wafer region statistically. Of course, this value does not always have to be six and it is needless to say that another value may be used in order to bring about the effect of the present embodiment. Since the number of allowable false alarms does not always have to be less than one, there is a possibility that another magnification will be selected.

As mentioned above, according to the present embodiment, illumination light is efficiently used, so that diffracted light from the pattern such as the LSI pattern in the substrate can be reduced by the spatial filter and the illumination direction. Moreover, the threshold is set low every position where the variation in the chip differs to thereby make it possible to extract only the defect to be desirably detected by the defect classification, which brings about an effect that the foreign material and the defect on the substrate such as the LSI wafer can be detected with high sensitivity and high throughput. Furthermore, the present invention brings about an effect that high sensitive TDI sensor or CCD line sensor is used to allow high-sensitive and high-speed detection of fine foreign materials and defects existing on the surface of the inspecting object 1 in which the repetition pattern and non-repetition pattern are mixed.

Moreover, the present invention brings about an effect that the threshold level as a criterion is set to optimum sensitivity so as to suppress an increase in false alarm in accordance with the various types of circuit pattern areas of the structure arranged on the inspecting object 1, thereby allowing inspection of a defect such a real foreign material.

Accordingly, it is possible to allow high-speed and high-accuracy inspection of the defects such as fine foreign materials on the inspecting object 1 in which the repetition pattern, non-repetition pattern, and no pattern are mixed. Moreover, it is possible to implement the inspection of all inspecting objects and the sampling inspection with a sufficient inspection frequency and construct the substrate manufacturing line with high efficiency. Furthermore, it is possible to classify types of detects such as the foreign materials existing in the various types of circuit pattern areas of the structure arranged on the inspecting object 1 according to the difference in distribution of orientation of scattered light from the defects. This makes it possible to detect only the defect to be noted with high sensitivity or specify the cause of the defect occurrence from the classification result of the detected defect. For this reason, it is possible to manufacture the semiconductor substrate with high efficiency and with good yield.

Modification Example

The present invention is not limited to the aforementioned embodiment, and, for example, the following modification may be possible.

Figure 18:
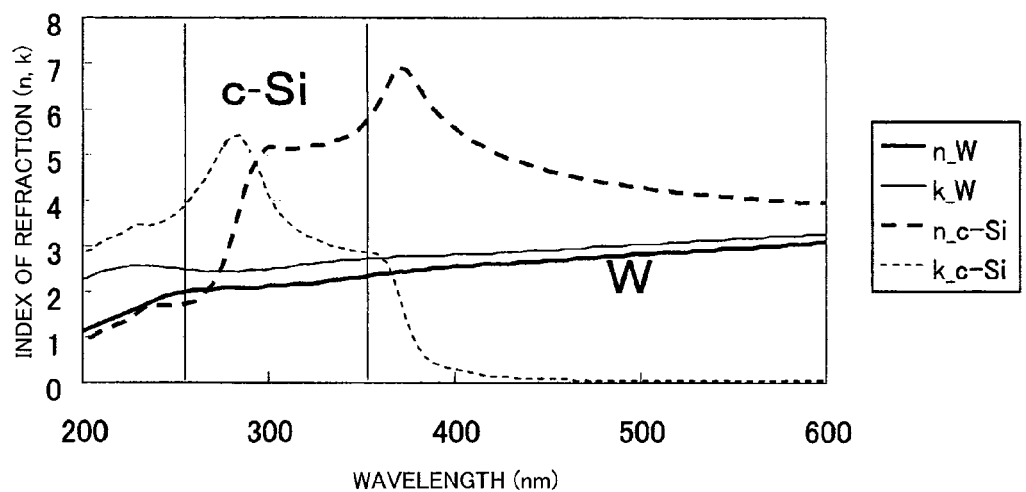
FIG. 18 is a view illustrating a wavelength dependence of a complex index of refraction of a semiconductor material to be used for an inspecting object.

(1) Although the laser beam source having a fundamental wave is used as the laser beam source 101 in the aforementioned embodiment, it is possible to use a harmonic laser. For example, a scattering coefficient also depends on an index of refraction, and the semiconductor material includes one whose index of refraction comes close to 1 in a specific wavelength region. FIG. 18 shows wavelength characteristics of complex indexes of refraction (n-jk) of tungsten W and crystallized silicon c-Si. Here, a thick solid line shows a real part n_W of index refraction of tungsten, and a thin solid line shows an imaginary part k_W. Moreover, a thick broken line shows a real part n_c-Si of index refraction of crystallized silicon, and a thin broken line shows an imaginary part k_c-Si. For example, in a short wavelength region in the vicinity of 200 nm, indexes of refraction of tungsten W and crystallized silicon c-Si come close to 1, and therefore when such materials are used, it is desirable to select a wavelength that does not belong to the wavelength region where the index of refraction comes close to 1.

Figure 19:
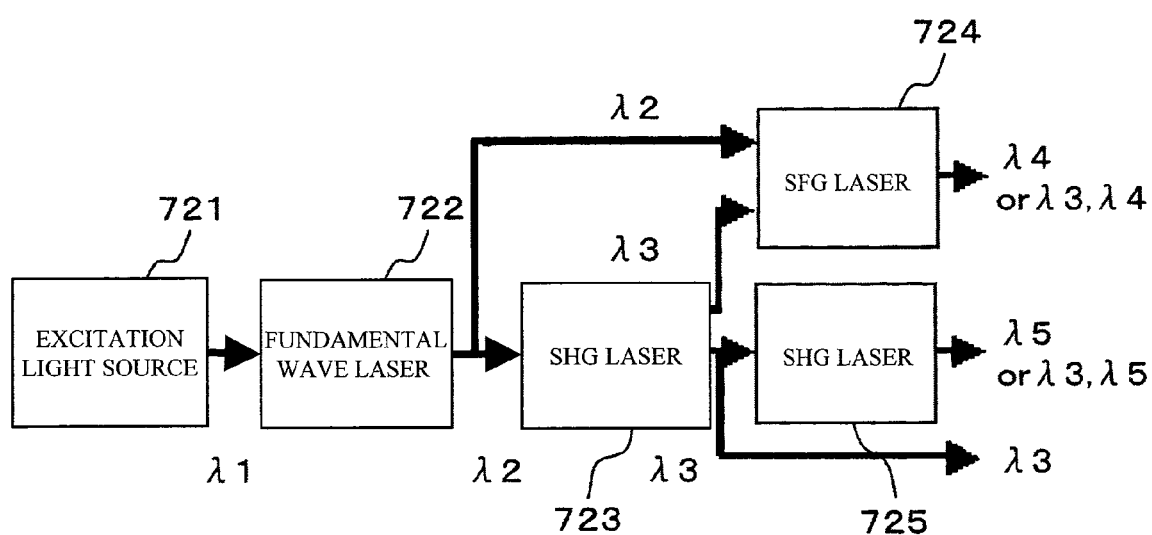
FIG. 19 is a view illustrating a configuration of a multi-wavelength light source to be used in an illumination optical system.

Note that, in case of using laser beam source such as YAG laser, in addition to use it as a fundamental laser, it can be used as shown in FIG. 19. For example, the second harmonics (lambda 3) and the fourth harmonics (lambda 5) can be generated by the wavelength conversion of the fundamental wave (lambda 2) of the YAG laser. Further more, the third harmonics (lambda 4) can be obtained by sum-frequency generation of the fundamental wave and the second harmonics. Moreover, combination of these, namely, a combination of the second harmonics and the third harmonics, a combination of the second harmonics and the fourth harmonics, a combination of the second harmonics and the third harmonics and the fourth harmonics are simultaneously outputted, so that an output result can be used as a multi-wavelength light source.

This makes it possible to reduce influences of dependence on index of refraction of material and thin film interference due to a film thickness of a transparent film such as an oxide film on the wafer and perform stable defect detection that does not depend on these conditions. It should be noted that the present embodiment has been explained by using some specific wavelengths, but that the wavelength does not have to be these wavelengths. In other words, as the laser beam source 101, there may be used other laser sources such as an Ar layer, a nitrogen laser, an He—Cd layer, an excimer laser or laser sources using those harmonics.

What is claimed is:

1. A defect inspection apparatus comprising:
a stage that runs with an inspecting object mounted thereon, the inspecting object including a circuit pattern having a group of lines parallel to each other formed therein;
an illumination optical system that illuminates a surface of the inspecting object with multiple pairs of slit beams, with each of the pairs comprising a first slit beam being a slit light so as to have a first inclined angle formed by the direction of the group of lines and a projection line of an optical axis of the slit beam to the inspecting object and another slit beam from a direction opposite to an incident direction of the slit beam on a plane;
a detection optical system that detects reflected and scattered light from the inspecting object by an image sensor;
a data processing section that extracts a signal indicating a defect such as a foreign material in response to a signal detected by the image sensor of the detection optical system; and
a defect classifying section that classifies the defect according to a difference in distribution of orientation of reflected and scattered light of the inspecting object.

2. The defect inspection apparatus according to claim 1, wherein in the illumination optical system, the optical axis of the slit beam has a second inclined angle relative to a normal direction of the inspecting object; and
in the detection optical system, the optical axis has a third inclined angle relative to the normal direction of the inspecting object.

3. The defect inspection apparatus according to claim 1, wherein the detection optical system is configured so that the optical axis of the first slit beam is set in a substantially normal direction relative to the surface of the inspecting object; and
a second inclined angle is formed by the optical axis of the detection optical system and the normal direction of the surface of the inspecting object.

4. The defect inspection apparatus according to claim 1, wherein the detection optical system has two optical systems in one of which the optical axis is set in a substantially normal direction relative to the surface of the inspecting object, and the other one of in which the optical axis has a third inclined angle relative to the normal direction of the inspecting object.

5. The defect inspection apparatus according to claim 1, wherein the stage runs perpendicular or parallel to the group of lines; and
the illumination optical system provides illumination in such a way that a longitudinal direction of the first slit beam is set to be a direction substantially perpendicular to the running direction of the stage.

6. The defect inspection apparatus according to claim 1, wherein the circuit pattern is a repetition pattern having a plurality of same circuit patterns;
the image sensor generates a repetition signal based on the repetition pattern; and
the data processing section includes:
a criterion setting section that calculates a variation in the repetition signal to set a criterion based on the calculated variation; and
an extraction section that extracts a signal indicating a defect such as a foreign material from the signal detected by the image sensor according to the criterion set by the criterion setting section.

7. The defect inspection apparatus according to claim 1, wherein the illumination optical system is configured to use a laser beam source to generate the first slit beam.

8. The defect inspection apparatus according to claim 1, further comprising:
a white illumination optical system that provides incoherent white light from a direction inclined to a normal of the inspecting object.

9. The defect inspection apparatus according to claim 1, wherein a spatial filter is used to detect a difference in distribution of reflected and scattered light of the inspecting object.

10. The defect inspection apparatus according to claim 1, wherein the image sensor is a TDI sensor.

11. The defect inspection apparatus according to claim 1, wherein in the illumination optical system, an inclination of the optical axis of the slit beam on a plane is 45 degrees relative to the direction of the group of lines.

12. A defect inspection apparatus comprising:
a stage that runs with an inspecting object mounted thereon, the inspecting object including a circuit pattern having a group of lines parallel to each other formed therein;
an illumination optical system that illuminates a surface of the inspecting object with a slit beam being a slit light so as to have a first inclined angle formed by the direction of the group of lines and a projection line of an optical axis of the slit beam to the inspecting object;
a detection optical system that detects reflected and scattered light from the inspecting object by an image sensor;
a data processing section that extracts a signal indicating a defect such as a foreign material in response to a signal detected by the image sensor of the detection optical system; and
a defect classifying section that classifies the defect according to a difference in distribution of orientation of reflected and scattered light of the inspecting object;
wherein the image sensor includes:
a storage section that stores an electrical charge generated by light receiving;
a current path that, when the stored electrical charges exceed a certain amount, makes the charges exceeded the certain amount flow; and
a reading section that reads an amount of charges stored in a range up to the certain amount.

13. A defect inspection apparatus comprising:
a stage that runs with an inspecting object mounted thereon, the inspecting object including a circuit pattern having a group of lines parallel to each other formed therein;
an illumination optical system that illuminates a surface of the inspecting object with a slit beam being a slit light so as to have a first inclined angle formed by the direction of the group of lines and a projection line of an optical axis of the slit beam to the inspecting object;
a detection optical system that detects reflected and scattered light from the inspecting object by an image sensor;
a data processing section that extracts a signal indicating a defect such as a foreign material in response to a signal detected by the image sensor of the detection optical system; and
a defect classifying section that classifies the defect according to a difference in distribution of orientation of reflected and scattered light of the inspecting object,
wherein the illumination optical system illuminates a plurality of areas on the inspection object, the detection optical system separately detects light scattered at the areas substantially forward and light scattered substantially backward from reflected and scattered light obtained from the defect existing on the surface of the inspecting object illuminated at plural portions by the illumination optical system, and the defect classifying section classifies the defect according to the output from the data processing section.

14. The defect inspection apparatus according to claim 1, further comprising:
a spatial filter in which at least one of a forward side and a backward side of a position irradiated with the slit beam are open such that light scattered substantially forward and light scattered substantially backward is detected and detected defects are classifiable with the spatial filter.

15. A defect inspection method, comprising:
running a stage mounting an inspecting object, on which a circuit pattern having group of lines parallel to each other is formed, in perpendicular or parallel to the group of lines;
illuminating a surface of the inspecting object with multiple pairs of slit beams, with each of the pairs comprising a first slit beam such that the direction of the group of lines and a projection line of an optical axis to the inspecting object form an inclined angle and a second slit beam from a direction opposite to an incident direction of the first slit beam on a plane, and that a longitudinal direction is set to be a direction substantially perpendicular to the running direction of the stage,
detecting reflected and scattered light from the inspecting object by an image sensor;
signal processing which extracts a signal indicating a defect such as a foreign material in response to a signal detected by the image sensor of the detection optical system; and
classifying the defect according to a difference in distribution of orientation of reflected and scattered light of the inspecting object.

16. The defect inspection method according to claim 15, further comprising:
performing signal processing for calculating a variation in response to the signal obtained by any one of the detection from an area where the same circuit pattern is formed and an area in the vicinity thereof, and then for extracting a defect from the signal detected by the image sensor according to a criterion set based on the calculated variation.

17. The defect inspection method according to claim 15, further comprising:
performing signal processing for extracting a defect from the signal detected by the image sensor according to a criterion set at each type of areas that form the circuit pattern.

* * * * *